(12) United States Patent
Burton

(10) Patent No.: US 6,575,902 B1
(45) Date of Patent: Jun. 10, 2003

(54) VIGILANCE MONITORING SYSTEM

(75) Inventor: David Burton, Camberwell (AU)

(73) Assignee: Compumedics Limited (AU)

( * ) Notice: Subject to any disclaimer, the term of this patent is extended or adjusted under 35 U.S.C. 154(b) by 0 days.

(21) Appl. No.: 09/890,324

(22) PCT Filed: Dec. 24, 1999

(86) PCT No.: PCT/AU99/01166

§ 371 (c)(1), (2), (4) Date: Jul. 26, 2001

(87) PCT Pub. No.: WO00/44580

PCT Pub. Date: Aug. 3, 2000

(30) Foreign Application Priority Data

| Jan. 27, 1999 | (AU) | ................................................ PP 8325 |
| Oct. 29, 1999 | (AU) | ............................................ PQ 3740 |

(51) Int. Cl.[7] ................................................ A61B 5/00
(52) U.S. Cl. ........................ 600/300; 600/306; 600/500; 600/544; 600/545; 600/546; 600/558; 600/595; 340/575
(58) Field of Search ................................. 600/300–301, 600/481, 485, 500–503, 529–538, 544–547, 306, 558, 595; 340/575, 576

(56) References Cited

U.S. PATENT DOCUMENTS

| 3,953,831 A | | 4/1976 | Estrada ........................... 340/52 |
| 4,259,665 A | | 3/1981 | Manning ..................... 340/575 |
| 4,928,090 A | | 5/1990 | Yoshimi et al. ............... 340/575 |
| 5,311,877 A | | 5/1994 | Kishi ........................... 128/732 |
| 5,574,641 A | * | 11/1996 | Kawakami et al. ............. 701/1 |
| 5,689,241 A | * | 11/1997 | Clarke, Sr. et al. .......... 340/575 |
| 5,813,989 A | | 9/1998 | Saitoh et al. ................. 600/484 |
| 5,813,993 A | | 9/1998 | Kaplan et al. ............... 600/544 |
| 5,846,206 A | * | 12/1998 | Bader ........................... 600/534 |
| 5,917,415 A | * | 6/1999 | Atlas ........................... 340/575 |
| 5,999,846 A | | 12/1999 | Pardey et al. ................ 600/544 |
| 6,126,595 A | * | 10/2000 | Amano et al. ............... 600/300 |
| 6,167,299 A | * | 12/2000 | Galchenkov ................. 600/547 |
| 6,218,947 B1 | * | 4/2001 | Sutherland .................. 340/576 |
| 6,353,396 B1 | * | 3/2002 | Atlas ........................ 240/693.9 |

FOREIGN PATENT DOCUMENTS

| CA | 2201694 | 10/1997 | ......... A61B/5/0476 |
| EP | 0713675 | 5/1996 | ............ A61B/5/18 |
| EP | 0773504 | 5/1997 | ........... G06F/19/00 |
| GB | 2284582 | 6/1995 | ........... G08B/21/00 |
| JP | 5092039 | 4/1993 | .......... A61M/21/00 |
| JP | 7079803 | 3/1995 | ........... A43B/13/02 |
| JP | 8140949 | 6/1996 | ......... A61B/5/0245 |

* cited by examiner

*Primary Examiner*—Robert L. Nasser
*Assistant Examiner*—Patricia Mallari
(74) *Attorney, Agent, or Firm*—Fulbright & Jaworski L.L.P.

(57) ABSTRACT

Apparatus for determining a vigilance state of a subject such as a driver of a vehicle or the like. The apparatus includes means (1 to 11) for monitoring one or more physiological variables such as EEG, EMG and EOG signals associated with the subject. The apparatus also includes means (13 to 16) for deriving from the one or more variables data representing physiological states of the subject corresponding to the or each variable and means (17) for determining from the data with the vigilance state of the subject is below a predetermined threshold. The apparatus may include means for intervening with the control of the vehicle in the event that the vigilance state of the driver is below the predetermined threshold.

27 Claims, 24 Drawing Sheets

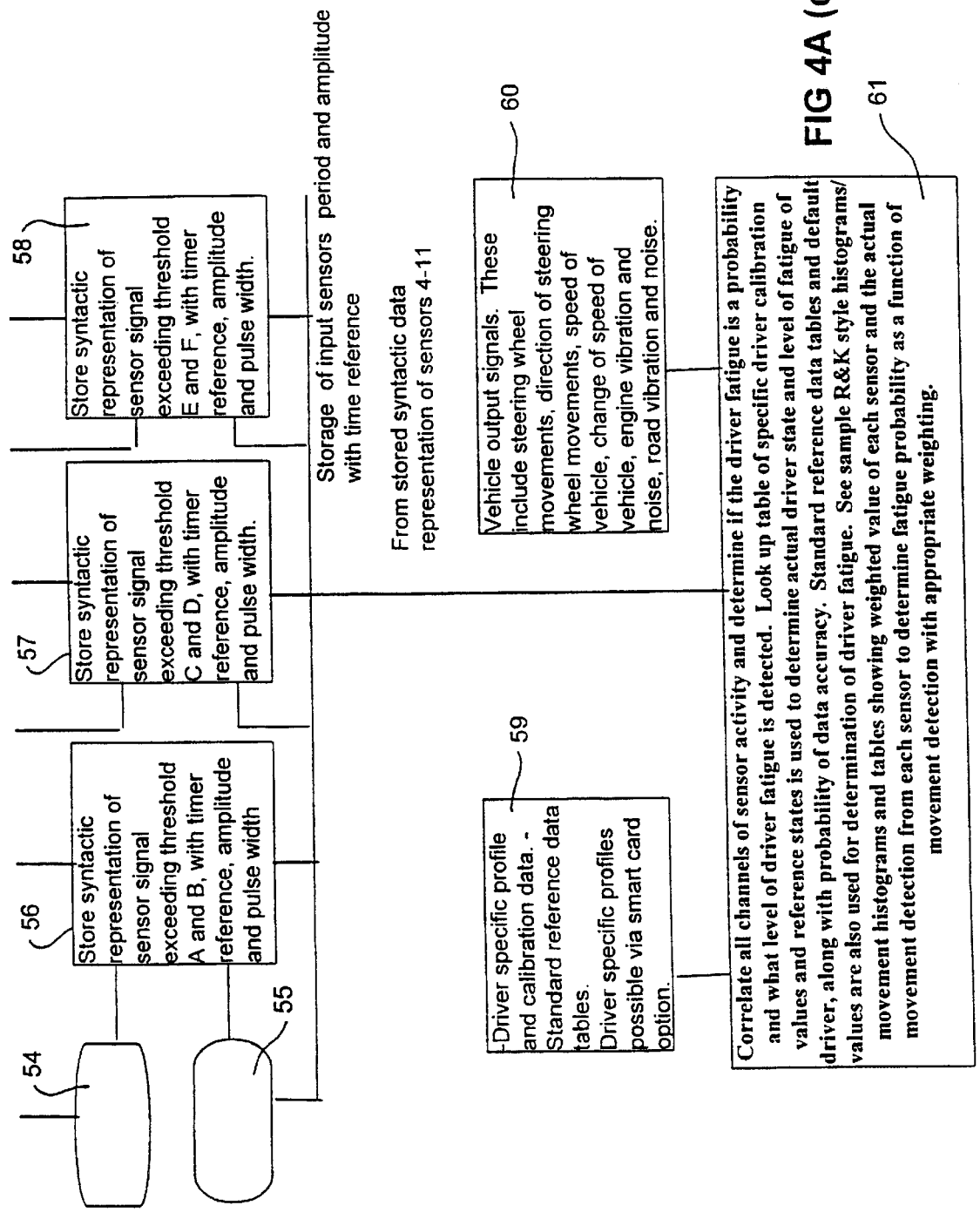

FIG 5
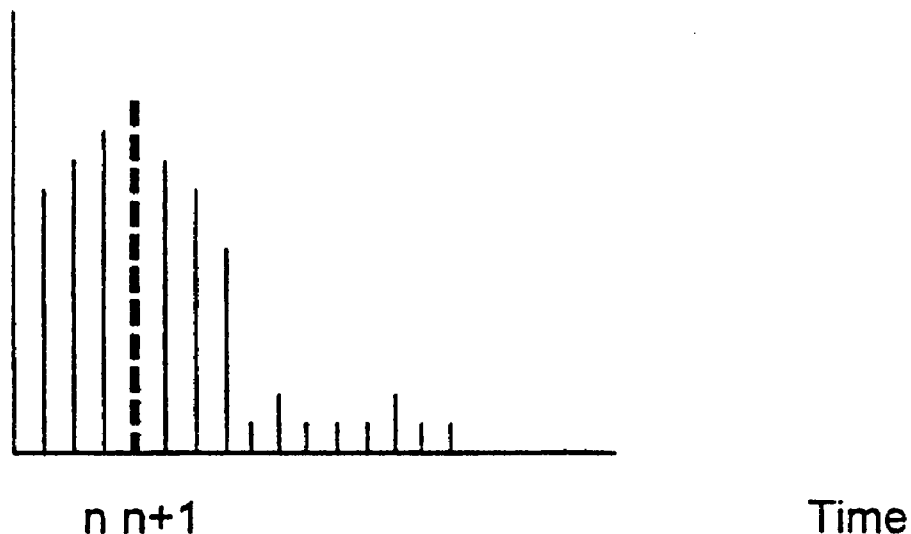
Sensor Signal 1
Number of movements
n n+1                                              Time
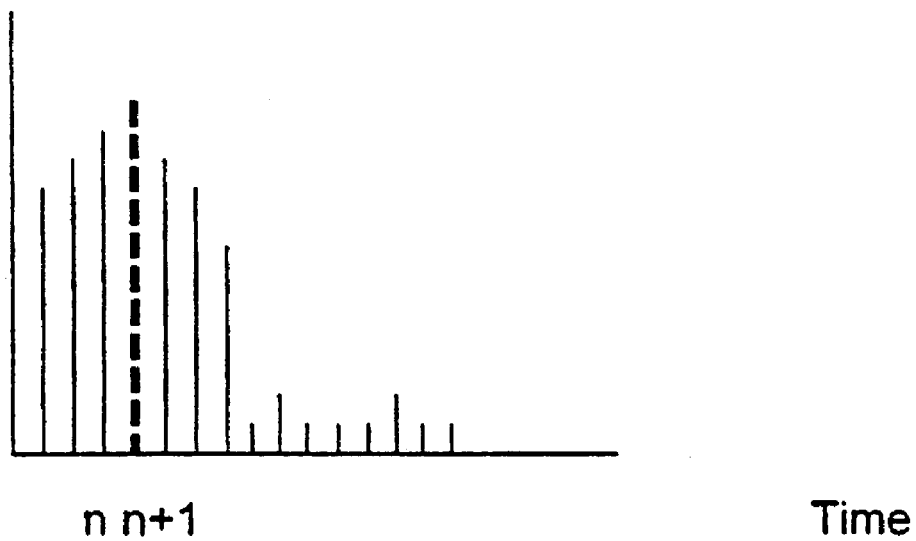
Sensor Signal 2
Number of movements
n n+1                                              Time

FIG 5 (cont.)
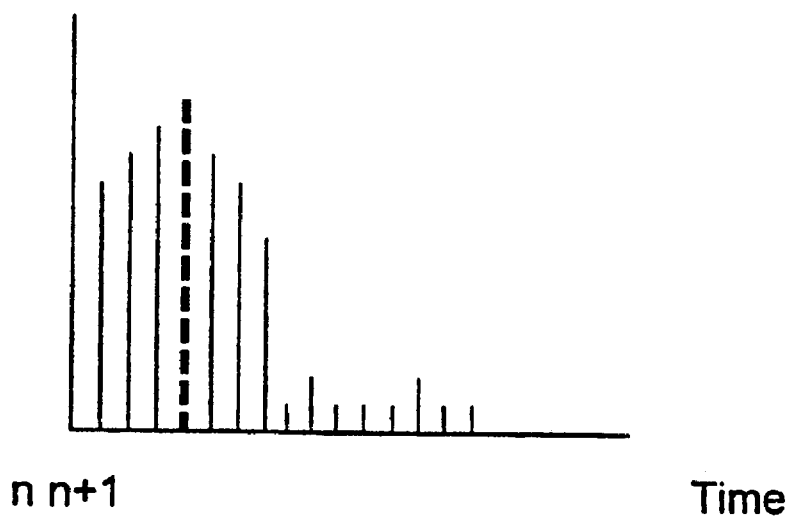
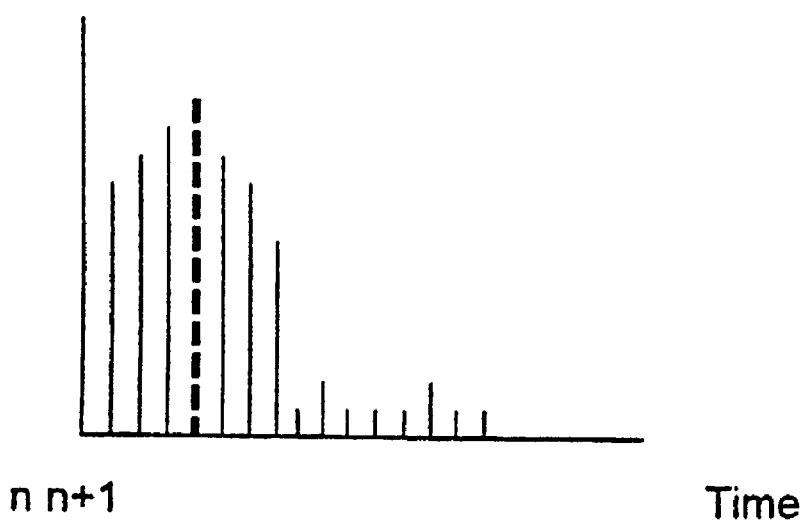

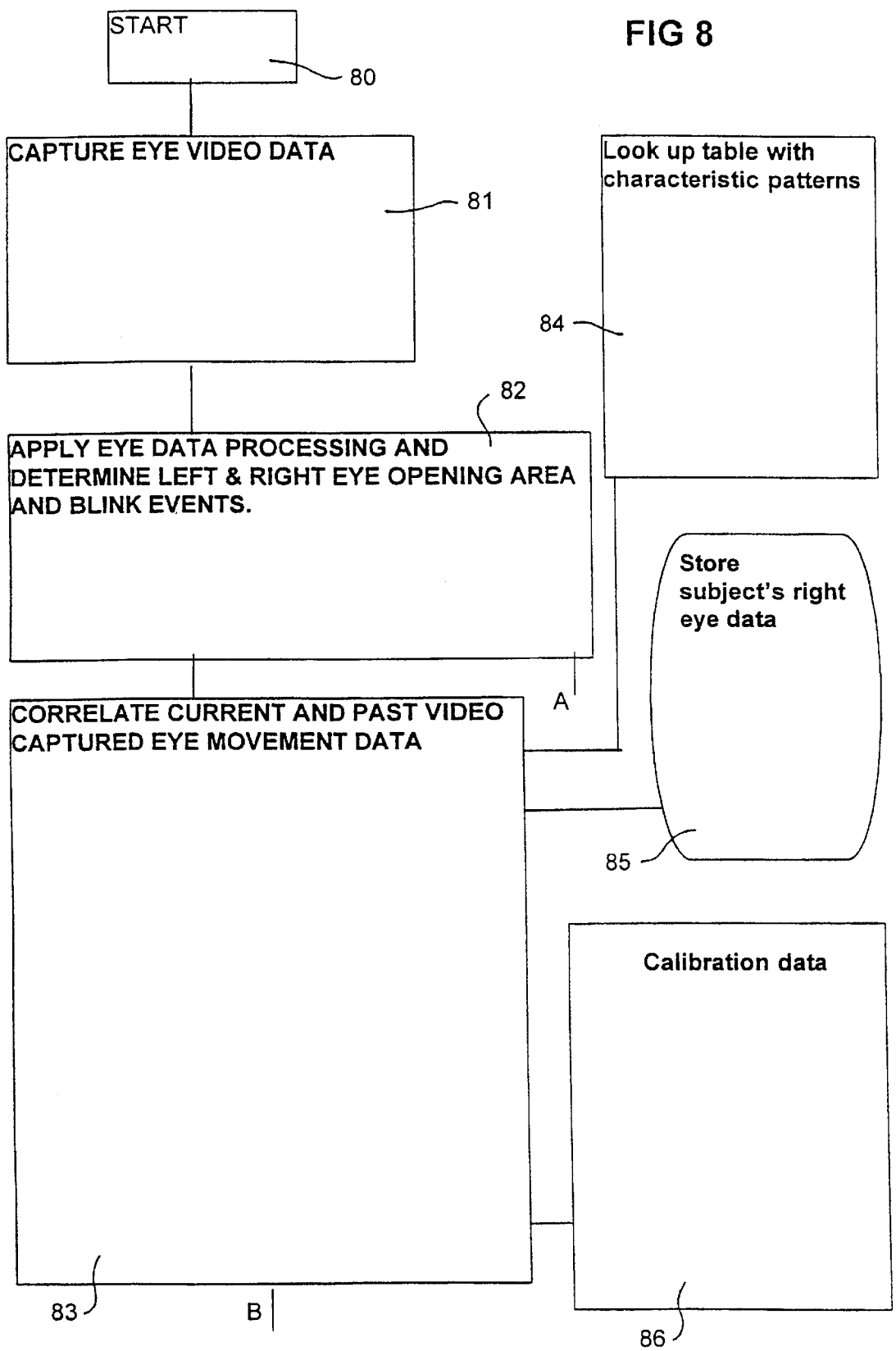

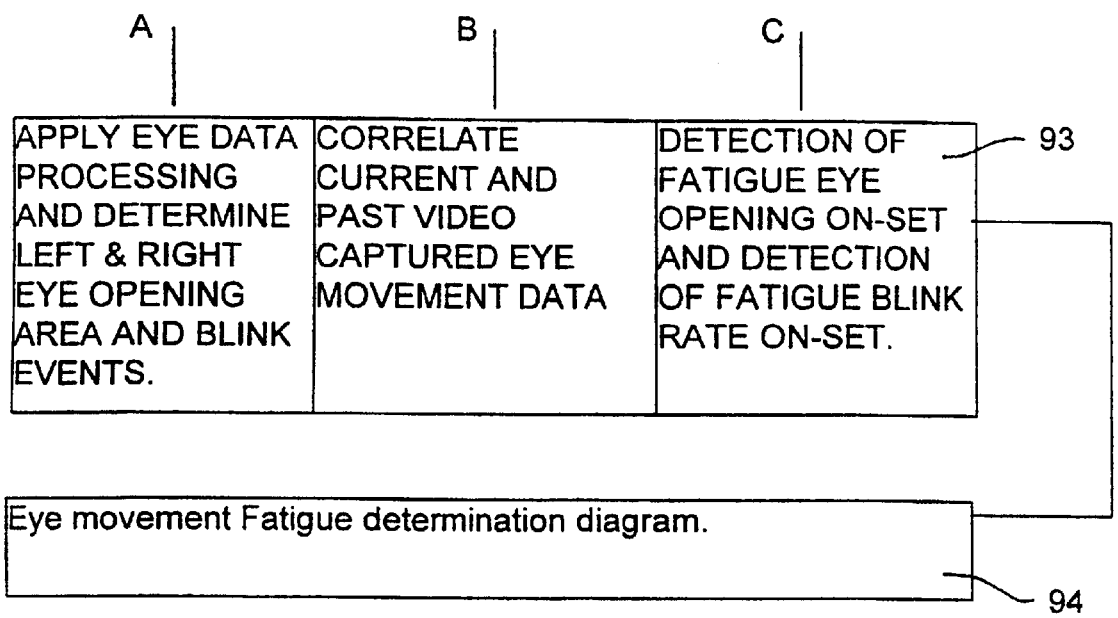
FIG 8 (cont. 2)

**LEFT
Eye opening height**
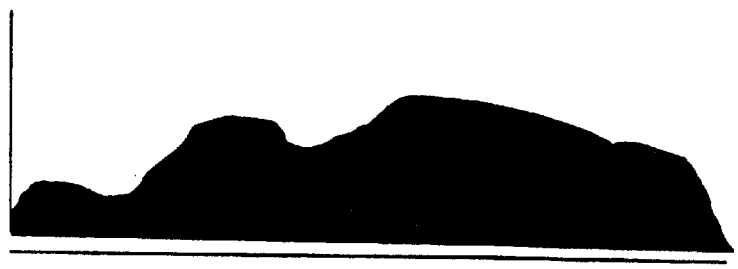
Secondary EOG data.
**RIGHT
Eye opening height**
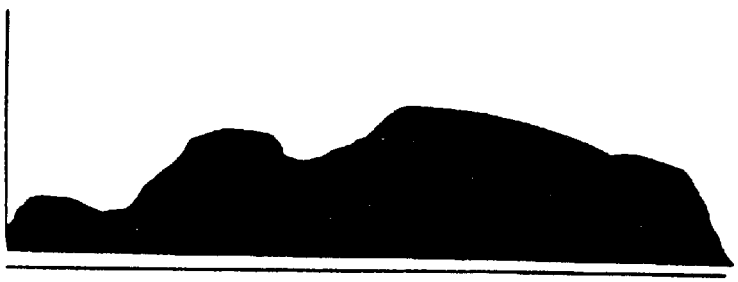
Secondary EOG data.
FIG 9

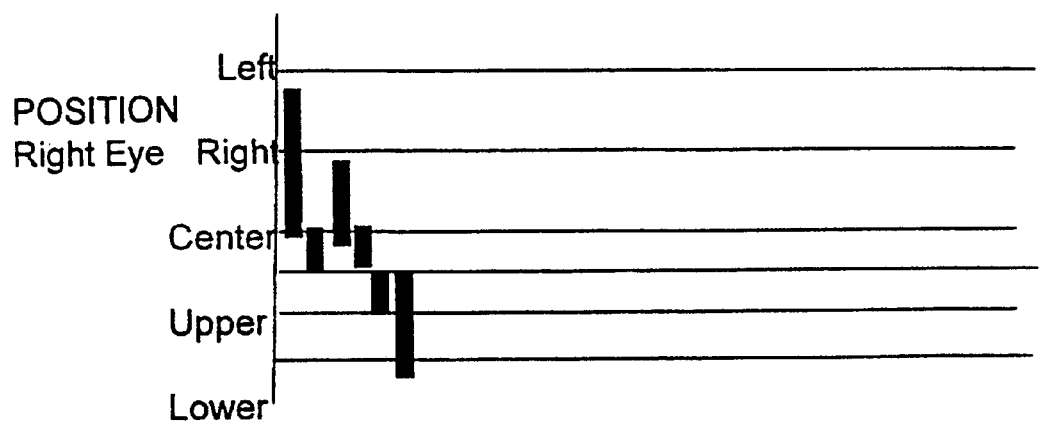
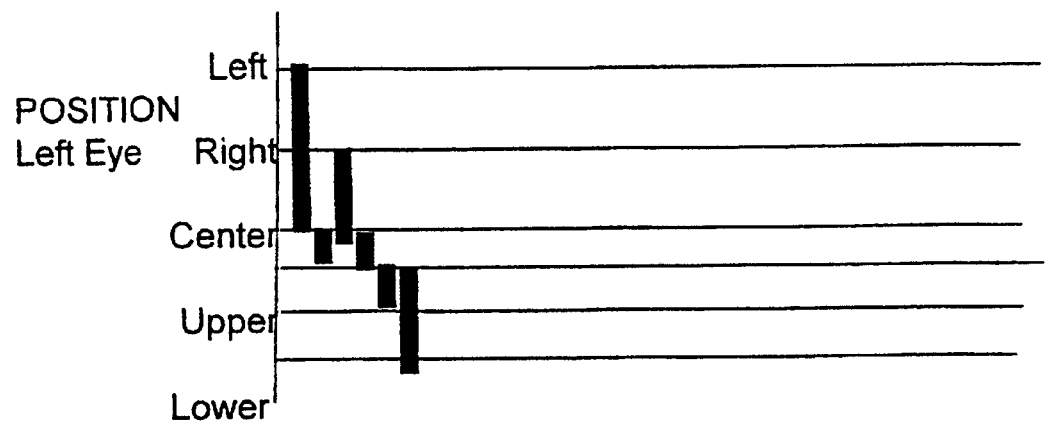
FIG 10

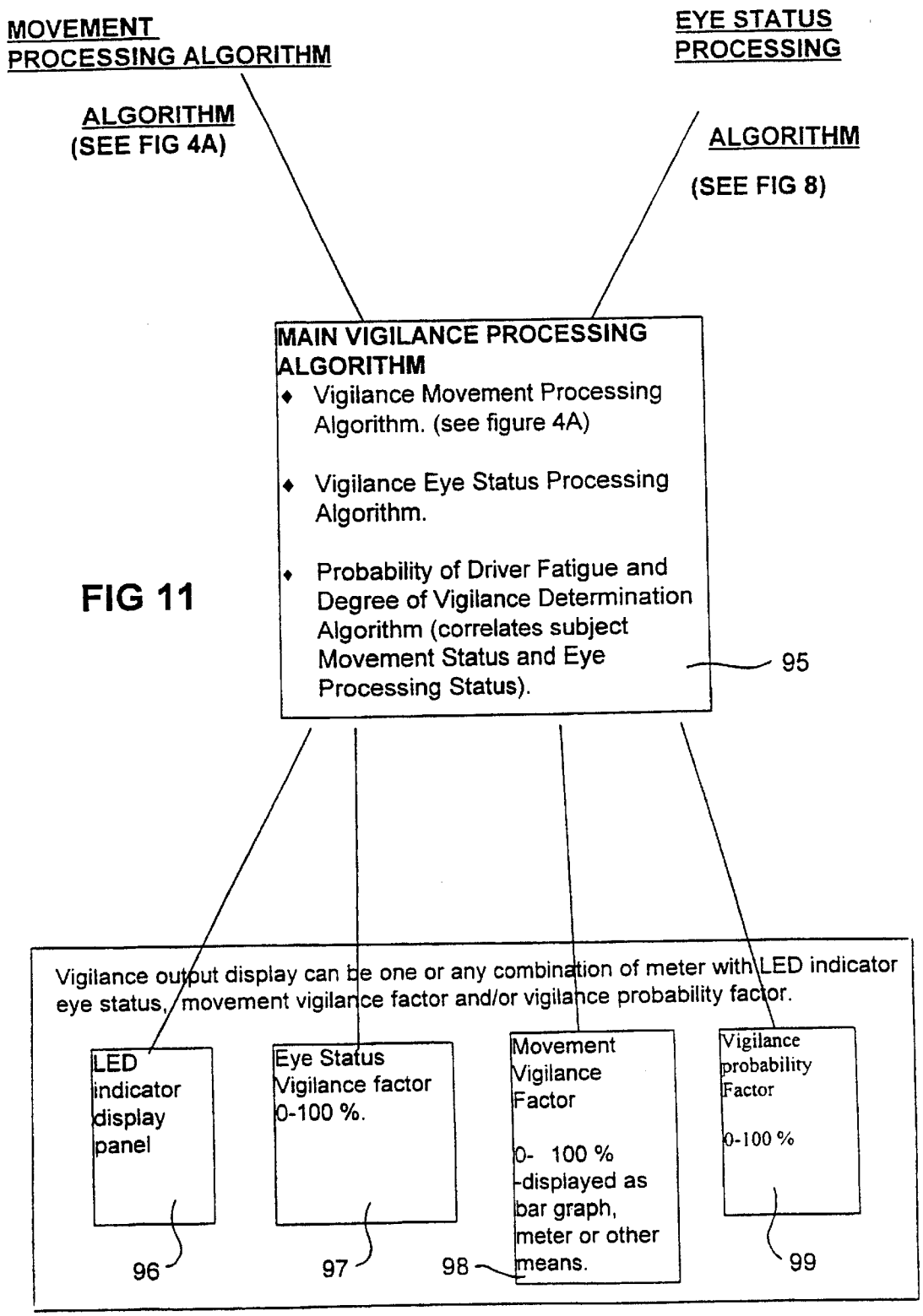

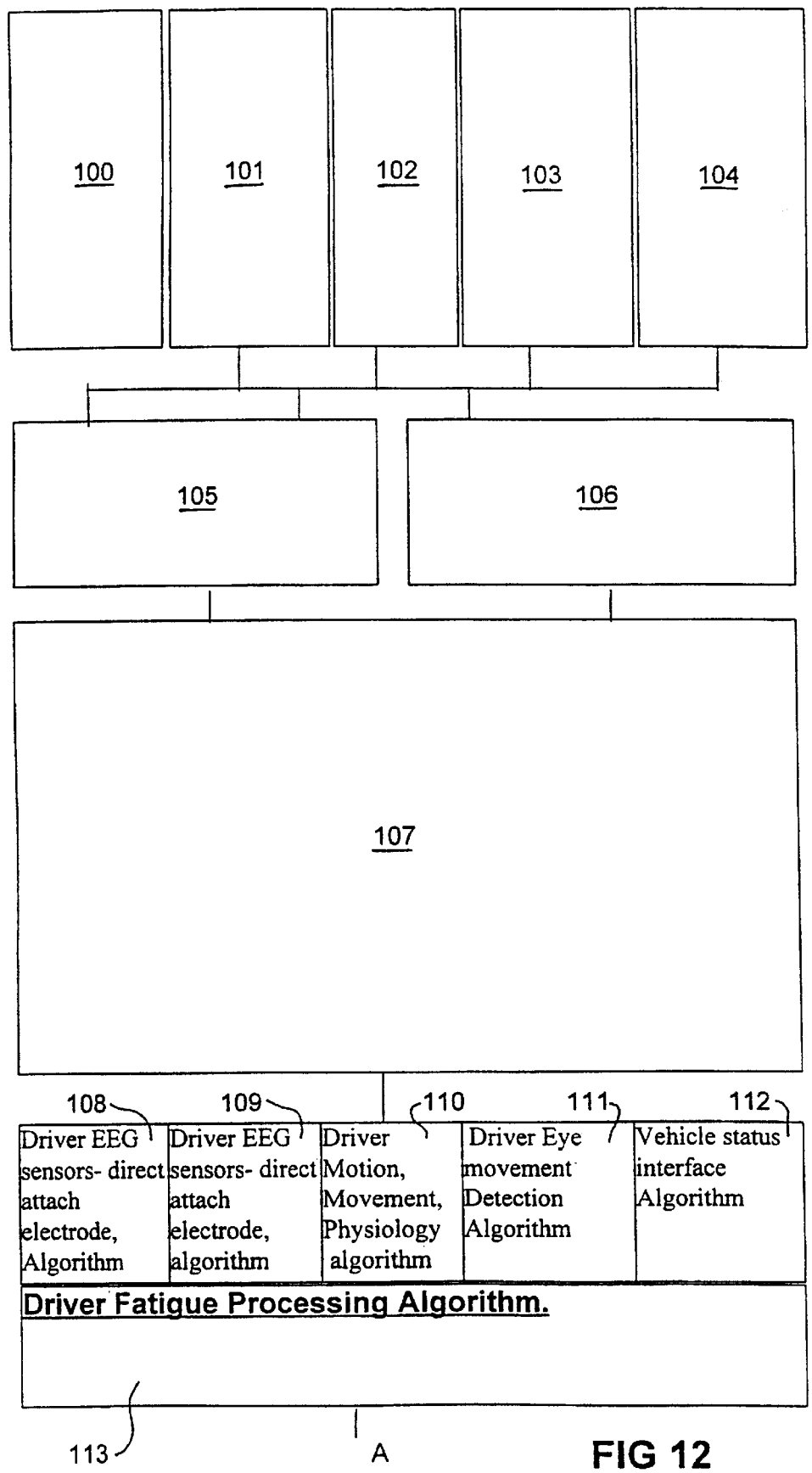

VIGILANCE MONITORING SYSTEM

CROSS REFERENCE TO RELATED APPLICATIONS

This patent application for U.S. Letters Patent relates to and incorporates by reference the contents of International application No. PCT/AU99/01166 and this application for U.S. Letters Patent hereby claims priority under 35 U.S.C. Section 365 to Jan. 27, 1999, the priority date of said International application.

The present invention relates to a vigilance monitoring system. In particular the invention relates to a system for monitoring, recording and/or analysing vigilance, alertness or wakefulness and/or a stressed state of an operator of equipment or machinery in a variety of situations including situations wherein the degree of vigilance of the operator has implications for the safety or well being of the operator or other persons. A typical application may include monitoring the driver of a vehicle or pilot of an aircraft, although the invention also has applications in areas involving related occupations such as train drivers and operators of equipment such as cranes and industrial machinery in general, and where lack of operator vigilance can give rise to harmful social or economic consequences.

The system of the present invention will be described herein with reference to monitoring a driver of a vehicle nevertheless it is not thereby limited to such applications. For example, other applications may include monitoring routine, acute or sub-acute physiological parameters of a person or subject in a home, work, clinic or hospital environment. The monitored parameters may include cardiac, respiratory and movement parameters as well as parameters relating to apnea events, subject sleep states or sudden death syndrome on-set.

The monitoring system is designed, inter alia, to provide non-invasive monitoring of a driver's physiological data including movement activity, heart activity, respiration and other physiological functions. The monitored physiological data may undergo specific analysis processing to assist in determining of the driver's state of vigilance. The system is designed to detect various states of the driver's activity and detect certain conditions of driver fatigue or relaxation state that could lead to an unsafe driving condition or conditions.

The system of the present invention includes means for gathering movement data associated with the driver. The movement gathering means may include a plurality of sensors such as touch sensitive mats placed in locations of the vehicle that make contact with the driver, such as the seat, steering wheel, pedal(s), seat belt or the like. Each location may include several sensors or mats to more accurately monitor movements of the driver.

Signals from the various sensors/mats may be processed and analysed by a processing means. The processing means may include a digital computer. The processing means may be programmed to recognize particular movement signatures or patterns of movement, driver posture or profile and to interpret these to indicate that vigilance has deteriorated or is below an acceptable threshold. The processing means may include one or more algorithms.

The sensors or mats may include piezoelectric, electrostatic, piezo ceramic or strain gauge material. The latter may be manufactured by separating two conductive materials such as aluminium foil with an electrolyte material which is capable of passing AC but not DC current. In one form the sensors or mats may include Capacitive Static Discharge (CSD) or Polyvinylidene fluoride (PVDF) material. The sensors/mats may be covered with a non-obtrusive, flexible surface which is capable of detecting pressure and/or monitoring electrophysiological activity.

The pressure detecting capability may be used for detecting driver movement. The or each sensor may produce an output signal that represents the magnitude of the pressure or force that is applied to the sensor. The or each pressure signal may thus represent an absolute or quantitative measure of pressure applied to the sensor. The electrophysiological activity may include electrical signals generated by the body of the driver eg. electrical muscle activity and/or pulse activity.

The sensors or mats may be located in various parts of a vehicle. The seat of the driver may be divided into several sections such as upper or back and lower or seat. The upper or back section may include sensors in the top edge, centre and base. The lower or seat section may include sensors in the front edge, centre and rear. The or each sensor may include CSD or PVDF material, The steering wheel may include a plurality of sensors. The steering wheel may be divided into eight zones such as upper, upper left, upper right, left, right, lower left, lower right and lower. At least one sensor may be associated with each zone. The or each sensor may include CSD or PVDF material.

The floor covering such as carpet may include a plurality of sensors. The floor covering or carpet may be divided into a plurality of zones. At least one sensor may be associated with each zone. The or each sensor may include CSD or PVDF material.

The accelerator, clutch and brake pedals may include a plurality of sensors. Each pedal may be divided into a plurality of zones such as upper, middle and lower. At least one sensor may be associated with each zone. The or each sensor may include CSD, PVDF or other movement sensitive material.

The seat belt may include one or a plurality of sensors. In one form a sensor or sensors may be embedded in the fixed (i.e. non-retractable) section of the seat belt. The or each sensor may include CSD or PVDF material.

In some embodiments a head tilt device incorporating a positional switch or the like may be associated with the drivers cap, glasses or goggles or may be arranged to clip over the drivers ear or glasses. The head tilt device may be adapted to provide a signal or data which alters in accordance with the position of the driver's head. Alternatively a radio tracking device may determine and track a subject's head movements.

In critical applications of vigilance monitoring including applications involving pilots of aircraft, persons responsible for navigating/controlling shipping and drivers of road or rail transport it may be desirable to utilize more comprehensive methods of vigilance monitoring. The latter may include techniques used in conventional sleep monitoring. A head band and/or chin band sensor may be used to monitor EEG, EMG and EOG signals. The head band sensor may include separate left and right frontal zones and left and right eye zones. The sensor may include CSD or PVDF material or other material sensitive to measuring patient skin electrical surface variations and/or impedance.

Various sensors/techniques may be adapted for monitoring eye movement including those based on reflected light, electric skin potential, contact lenses, limbus tracking, video imaging and magnetic induction. The sensors/techniques may include EOG electrodes, infrared detection of eye movements and/or video tracking and processing of eye movements. The sensors/techniques may be adapted for monitoring the left eye only or the right eye only or both eyes.

Raw data which is collected from the various sensors positioned around the vehicle may be filtered and amplified prior to processing and analysis. A significant purpose of the processing and analysis is to determine the driver's state of vigilance, alertness or wakefulness. In some embodiments, the system may be adapted to effect remedial action, ie. the system may take steps to alert the driver or to actively intervene in the control of the vehicle, when it is deemed that such action is warranted or desirable.

Processing of data may be performed in several stages, including primary, secondary and tertiary analysis.

Primary analysis refers to processing of raw data from the various sensors. This raw data may be filtered and amplified prior to analog to digital conversion. Primary analysis may be adapted to determine valid body movements of the driver as distinct from spurious signals and artefacts due to environmental factors including noise.

Valid body movements may be determined by applying a combination of processing techniques including:

1. signal threshold detection whereby signals below or above a pre-determined threshold are ignored and/or classified as noise or artefact,
2. frequency filtering whereby high-pass, low-pass and notch filters are adapted to remove noise and artefact signals,
3. signal compression whereby data is minimized by presenting main data points such as signal peaks, troughs, averages and zero crossings,
4. half period, amplitude analysis of signals, including analysis as disclosed in AU Patent 632932 entitled "Analysis System for Physiological Variables", assigned to the present applicant, the disclosure of which is incorporated herein by cross reference.

Threshold detection may facilitate distinguishing random and non-significant electrical noise (typically spikes of small duration) relative to signals representing valid or actual body movements. Threshold detection may apply to both amplitude and duration of the signals. The relevant threshold(s) may be determined from clinical trials and/or historical data. Where the detection is based on amplitude it may be determined in both negative and positive phases of the signal. Amplitude detection may be based on a measurement of the peak-to-peak signal. Alternatively, the positive and negative peak amplitudes can be measured separately. Threshold detection may be combined with a form of zero-base line detection so that electronic offsets do not adversely affect the accuracy of threshold detections. Each body movement which exceeds the predetermined amplitude and/or duration may be classified as an event for further processing.

Secondary analysis may be adapted to process the results of primary analysis. Secondary analysis may process data for the purpose of presentation and/or display. Data may be displayed or printed in a tabular, graphical or other format which facilitates interpretation of the data. One purpose of the representation and/or display is to represent a driver's state of vigilance and/or fatigue. In one form each event identified during primary analysis may be counted for a fixed period of time or epoch. The fixed period of time may be 30 seconds or 60 seconds, or other period which is adequate for determining body movement trends. The count value or number of valid body movements in a given period (eg. 30 seconds) may be represented in a display as, say, the length of a vertical bar.

Where it is desired to display the energy or power associated with valid body movements in a particular epoch or time period, the average amplitude associated with each event may be indicated by the length of the vertical bar whilst the count value or number of valid body movements for each epoch may be represented by colouring the vertical bar. For example the colours green, blue, yellow, orange, red may indicate count values or movement numbers in ascending order ie. green indicating the lowest movement number for a particular epoch and red indicating the highest movement number for a particular epoch. Alternatively, data may be displayed on a 3 dimensional graph wherein for example the x dimension of the graph represents time or epochs, the y dimension represents the average amplitude, while the z dimension represents the number of events during a particular epoch. The above display techniques may facilitate interpretation of the number of valid body movements and the amplitude of those movements and association of this data with the driver's activity or state of vigilance, alertness or wakefulness.

It may also be relevant to measure the period of each individual body movement as this may provide an indication of the energy that is associated with the movement. For example, if a driver squeezes the steering wheel in a rapid response as distinct from gripping the wheel as part of a focussed steering manoeuvre, the pattern of signals in each case will be different. The rapid response may appear as a small cluster of movements/signals or as a single movement/signal with a relatively short duration or period of time. In contrast, the steering manoeuvre may appear as a larger cluster of movements/signals over a relatively longer period of time or as a single movement/signal having a relatively long duration.

The type of signal which may be expected (cluster or single movement/signal) will depend in part upon the type of sensor. For example, piezo ceramic or PVDF sensors may emit fewer clusters of signals but may emit signals with larger time periods in relation to the actual period of the movement which is being monitored. A capacitive electrostatic sensor is more likely to emit clusters of "spikes" being relatively short period signals. It may be necessary to record the energy level of each movement as this energy level may fall below a certain threshold when the driver is in a fatigued state. If, for example the driver has relaxed, then the energy of a body movement in the actions of driving may be significantly more subdued than in the case where the driver is alert, and his muscle activity is significantly greater. Therefore it may be useful to measure and record each and every body movement. This data could be displayed on high-resolution graphs where for example the X-axis represents ½ second periods and 960 lines make up each continuous section or 480 seconds (8 minutes). The largest amplitude signal in each ½ second period could then be displayed on the X-Axis. The Y-Axis on the other hand could be represented by a scale of amplitudes representing each body movement. This graph would be more precise in representing the actual signal level of each body-movement and the subsequent muscle status for a driver.

It may also be useful to detect events that are represented by groups of movements, where, for example, the groups of movements may be indicative of a driver activity of interest. Detection of groups of movements may include user configurable or preset values for;

the maximum time between consecutive body-movements in order to qualify as being counted as part of a periodic body-movement.

the number of consecutive body-movements that are required to qualify for a periodic movement.

the time period during which this number of body-movements must exist in order to qualify as a periodic body-movement.

Periodic measurement analysis can detect, for example, absence of movements which can be associated with a driver's fatigue.

Tertiary analysis may be adapted to process the results of secondary analysis. One purpose of tertiary analysis is to determine the status of a drivers state of vigilance, alertness or wakefulness. Tertiary analysis may process the results of secondary analysis to produce intermediate data and/or indicate trends in the data. The intermediate data and trends may be used to provide summary reports and further tabular and/or graphic representations of a drivers status or condition. The intermediate data may be processed by one or more vigilance algorithms to determine the status of a driver's vigilance, alertness or wakefulness. Intermediate data of various types may be derived and the vigilance algorithm(s) may make use of such data to determine the status of the driver. The intermediate data may include:

Rate of change of body movement detections

Rate of change of body movement amplitudes

Area under curve of time versus body movement, for various sequential epochs to detect trends of subject movement changes (amplitude or number of movements)

Correlation of sensor data for patterns of amplitude, energy and body movement changes that can be associated with driver fatigue Change in frequency of body movement signals Change in amplitude periods of body movement signals Change in phase relationships of body movement signals Relative phase relationship between each section and other types of sensor sections.

Following tertiary analysis the vigilance algorithm(s) may be adapted to correlate the intermediate data and/or apply combinational logic to the data to detect patterns of movement (or lack thereof) which, based on historical data or clinical trials, indicates that the driver is or may be excessively relaxed or is below an acceptable threshold of vigilance, alertness or wakefulness.

The vigilance algorithm(s) may incorporate one or more look up tables including reference movement data and default values associated with acceptable and unacceptable levels of driver fatigue. Histograms including movement histograms of the kind described in AU Patent 632932 based on the work of Rechitschaffen and Kayles (R & K) may be used as well as tables showing weighted values and actual movement data for each sensor.

The vigilance algorithm(s) may determine a vigilance probability factor (0–100%) as a function of weighted movement data values.

Upon detecting a vigilance probability factor which is below an acceptable threshold, the system may be arranged to intervene in the control of the vehicle or to alert the driver of the vehicle and/or other vehicles. Vehicle control intervention may include restriction of speed, controlled application of brakes, cutting-off fuel and/or disabling the accelerator pedal. Driver alerting intervention may include use of sprays designed to stimulate the driver, vibrating the steering wheel, seat belt or floor area in the vicinity of the driver, an audible alarm and/or use of bright cabin lights. The driver can also be alerted by winding down the driver window and/or other effective alerting methods as may be applicable to each individual driver. Drivers of other vehicles may also be alerted by means of flashing hazard lights and/or sounding of a siren. Vehicle control intervention may be integrated with and form part of a vehicle control system or it may be interfaced to an existing vehicle control system. Vehicle control intervention may be interfaced with GSM or other communication systems to provide early warning indication that a driver or operator of equipment is in a stressed, fatigued or other undesirable condition that may be detected.

To assist differentiating normal and acceptable driver vigilance from fatigued or inappropriate driver conditions, calibration of the various sensor and transducer outputs is possible. Calibration can set the system's detection parameters in accordance with varying driver movement and other driver signals. Calibration is beneficial because driver sensor and signal outputs will vary with different drivers. Background noise will also vary with different vehicles. The need for calibration may be proportional to the critical nature of the driving or dependent on the level of accuracy required for fatigue monitoring and detection.

The need for calibration may to some extent be removed by utilizing artificial intelligence to distinguish baseline conditions for a drivers normal wakeful state to facilitate subsequent analysis and determining when a driver's state indicates fatigue or lapse of vigilance. Artificial intelligence may be embodied in one or more automated systems including one or more mathematical algorithms. Artificial intelligence includes the systems ability to self-learn or teach itself conditions associated with the driver which constitute normal or alert driving as distinct from conditions which constitute abnormal or fatigued driving.

Artificial intelligence may allow the driver of a specific vehicle to select a mode of operation during which the driver's movements during normal or wakeful driving are monitored and diagnosed in order to determine typical thresholds and correlations between various sensors, for the purpose of determining true fatigue states of the driver as distinct from alert states of the driver. Artificial intelligence may also facilitate adaptation of the vigilance algorithm(s), to the specific vehicle's background noise characteristics.

Artificial intelligence may include different response patterns for correlating movement data from the various sensors for distinguishing valid driver movements from environmental vibrations and noise. These may be classified and described by, for example, a look up table that records expected patterns or combinations of signals for different cases of environmental noise as distinct from driver generated signals. For example, if the driver moves his hand, signals from sensors in the steering wheel and arm sections of the seat may correlate according to a specific pattern. Alternatively, if the vehicle undergoes a severe or even subtle vibration due to road or engine effects, a broader range of sensors may be similarly affected and this may be manifested as amplitudes which follow predetermined correlation patterns. Signals from the sensors may increase in strength or amplitude according to the proximity of the source of the sound or vibrations. Where the source of the vibration is localized, this may manifest itself as a pattern of similar waveforms across the various sensors which reduce progressively in amplitude as the sensors distance from the source increases. For example, if the source of the vibration is road noise, the floor sensors may register maximum amplitude whereas the steering wheel sensors which are furthest from the road noise may register minimum amplitude.

The phase relationship of vibrations from various sources may also provide some guide as to the likely source of the vibrations. For example, if the vibrations emanate from the driver's movement then it is more likely that several signals with similar phase may be detected. On the other hand, if the signals have varying phase relationships, then it is more likely that the source of the vibrations giving rise to these signals is random as may be expected if the vibrations emanate from the vehicle environment.

Similar phase signals arising from driver movements may be distinguished from similar phase signals arising from artefacts or the vehicle environment by relating the environmental noise to sensors located near sources of expected noise in the vehicles, eg. engine noise, wheel noise, and other vibrations and noise. This may be detected by carefully locating microphones and vibration sensors in the vehicle.

Cancellation of environmental noise can be assisted by monitoring signals from the microphones and sensors with a view to applying the most effective signal cancellation techniques in order to reduce as much as possible the artefact or noise effects or unwanted signals within the vehicle environment.

One example of the application of noise cancellation techniques includes detection of the various road bumps and ignoring the effect of these bumps on the data being analysed from the various vehicle sensors of interest.

Another example of the application of noise cancellation techniques includes detection of various engine noises and application of a signal of opposite phase to the motor noise in order to cancel the artefact. One example of phase cancellation techniques which may be adopted is disclosed in PCT application AU97/00278, the disclosure of which is incorporated herein by cross-reference.

Other examples of noise cancellation include filtering wherein highpass, lowpass and notch filters may be used to assist artefact removal. Artificial intelligence may learn to ignore periodic signals from sensors in the vehicle as these are likely to arise from mechanical rotations within the vehicle, thus improving the separation of artefact signals from signals of interest, such as signals which indicate true driver movement.

Artificial intelligence may also learn to recognize changes in the driver's state which reflect changes in driver vigilance or wakefulness. Points of calculation and analysis of sensor data for the purpose of comparison and correlation with previously monitored data may include:

spectral analysis of signals with a range of consecutive time periods;

½ period time amplitude analysis of signals and other techniques used in conventional sleep analysis as disclosed in AU Patent 632932;

calculation of the number of movements per consecutive periods of time, wherein the consecutive periods of time may typically be, 1 second or ½ second;

calculation of average signal levels during periods of, say, 20 or 30 seconds;

calculation of total "area under the curve" or integration of sensor signals for a period of, say, 20 or 30 seconds;

correlation and relationship between various combinations of input sensor channels;

ECG heart rate and respiration signals, the latter signals providing an indication of the drivers wakeful state, as heart-rate and respiration signals during the sleep state are well documented in a number of medical journals.

Artificial intelligence may be applied in conjunction with pressure sensors in vehicle seats and/or seat belts to control air bag deployment. In this way air bag deployment may be restricted for children or validated with different crash conditions for children and adults. For example, if a child is not detected as being thrust forward by means of pressure data received from seat/seat belt sensors, deployment of air bags and possible air bag injury to the child may be avoided.

Deployment of air bags may generally be validated more intelligently by analysing data relating to passenger or driver posture, movement, thrust, body movement, unique driver or passenger 'yaw' etc.

The system may include means for testing a driver's response times. "Such tests may, if carried out at regular intervals, pre-empt serious driving conditions as can be brought about by driver fatigue or a lapse in vigilance. The testing means may be adapted to provide a simple method for prompting the driver and for testing the driver's response time. The response test may, for example, request the driver to respond to a series of prompts. These prompts may include requesting the driver to squeeze left or right hand sections of the steering wheel or squeeze with both left and right hands at the same time in response to a prompt. The means for prompting the driver may include, for example, LEDs located on the dash of the vehicle or other position that the driver is visually aware of. A left LED blinking may for example, prompt the driver to squeeze the left hand on the steering wheel. A right LED blinking may prompt the driver to squeeze the right hand on the steering wheel. The centre LED blinking may prompt the driver to squeeze both hands on the steering wheel. Alternatively two LEDs could be used in the above example, except that both LEDs blinking may prompt the driver to squeeze with both hands.

The drivers response or level of alertness may be detected by measuring the response time of the driver, where the response time is measured as the time between illumination of an LED and a correct response with the hand or hands. In a case where an inappropriate response time is detected (potentially signalling driver fatigue or onset of driver fatigue) the system can verify the results and alert the driver. The system may also determine the accuracy of the driver's responses to ascertain the status of the driver's vigilance.

A further example of means for testing the driver's response may include means for flashing random numbers on the windscreen. The driver may be prompted to respond by squeezing the steering wheel a number of times as determined by the number flashed. The numbers may be flashed on the screen at different locations relative to the steering wheel with the position of the hands on the wheel responding to the side of the screen where the flashes were detected. This type of test should be conducted only when the driver is not turning, changing gear, braking or performing other critical driving functions.

It is desirable to ensure that the driver response tests are not anticipated by the driver to more accurately detect the driver's state of vigilance. It is of course also important that the selected method of testing driver response, does not in any way distract the driver or contribute to the driver's lapse in concentration.

The system may be built into a vehicle sun visor as a visual touch screen display allowing a comprehensive visualisation of a drivers activity. The touch screen may include a color display for displaying movement/pressure outputs associated with each sensor. A display of the status of a plurality of sensors may provide a visual indication of a relaxed versus an active driver state.

According to one aspect of the present invention, there is provided apparatus for determining a vigilance state of a subject such as a driver of a vehicle or the like, said apparatus including:

means for monitoring one or more physiological variables associated with said subject;

means for deriving from said one or more variables data representing physiological states of said subject corresponding to the or each variable; and means for determining from said data when the vigilance state of said subject is below a predetermined threshold.

According to a further aspect of the present invention, there is provided a method for determining a vigilance state of a subject such as a driver of a vehicle or the like, said method including the steps of:

monitoring one or more physiological variables associated with said subject;

deriving from said one or more physiological variables data representing physiological states of said subject corresponding to the or each variable; and determining from said data when the vigilance state of said subject is below a predetermined threshold.

Preferred embodiments of the present invention will now be described with reference to the accompanying drawings wherein:

FIG. 5 shows sample outputs of data following secondary analysis by the system of FIG. 4A;

FIGS. 9 and 10 show examples of data produced by the system of FIGS. 7 and 8;

FIG. 11 is a flow diagram of the main vigilance processing algorithm;

Figure 1:
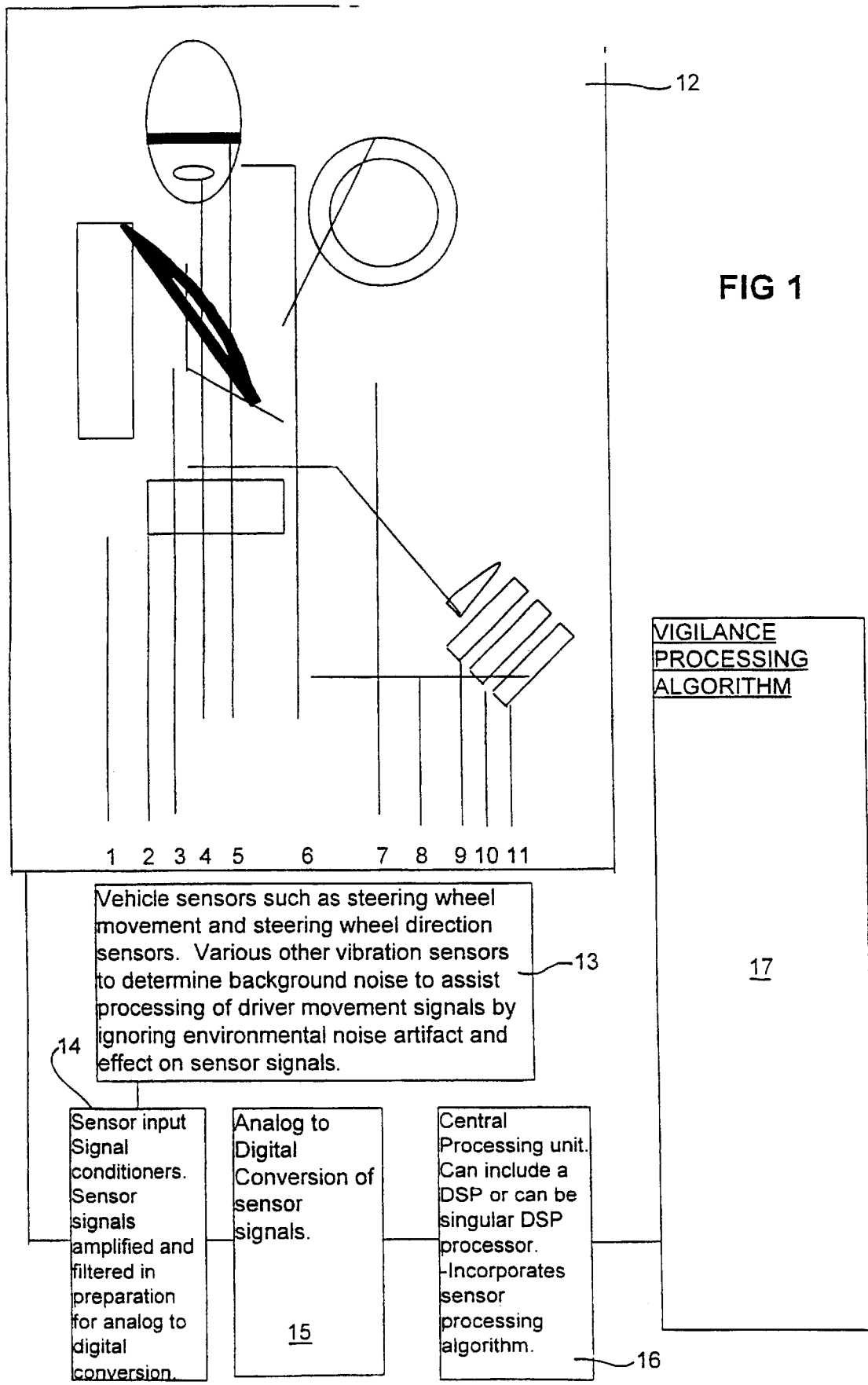
FIG. 1 shows a block diagram of a vigilance monitoring system according to the present invention.

Referring to FIG. 1, block 12 shows a plurality of sensors 1 to 11 associated with a vehicle and driver. The or each sensor may include piezoelectric or electrostatic material such as CSD or PVDF material. The material can be divided into plural sections of the driver's seat, for example. The various sensors are summarized below.

1. Upper Driver Seat Sensor

Drivers seat top edge of upper section
Drivers seat centre of upper section
Drivers seat base of upper section 2. Lower Driver Seat Sensor Drivers seat front edge of lower section
Drivers seat centre of lower section
Drivers seat rear of lower section 3. Driver Seat-belt Sensor Driver's seat-belt upper section
Driver's seat-belt lower section 4. Driver's Head Tilt Per Driver Cap or Similar Sensor The driver's head tilt per driver cap or a device to clip over drivers ear or as part of driving goggles or glasses. These sensors can be, for example, positional switch devices. The output from these positional devices is amplified, filtered and finally data acquisitioned and analysed. This sensor device is designed to output a signal or digital data which changes state in accordance with the tilt of the driver's head. By calibration of the system in accordance with normal driving conditions this output can correlate the normal driving condition with the fatigued driver condition.

5. Driver Headband Sensor

The driver headband sensors can be, for example, a Capacitive Static Discharge Material (CSDM) or PVD Material (PVDM) that can be divided into the various sections (as listed below) of the driver's headband sensor. The output from the various sensors is amplified, filtered and finally data acquisitioned and analysed. The headband material can contain conductive sections designed to pick-up the patient's electro-encephalograph (EEG) signals.

Driver Headband Sensor

Driver headband left frontal
Driver headband right frontal
Driver headband left eye
Driver headband right eye EEG, EMG and EOG Parameters Monitored in Critical Driving Conditions.

In some critical applications of vigilance monitoring, such as pilots of aircraft, personnel responsible for navigating and controlling ships, drivers of road or rail transport or passenger vehicles, it can be appropriate to apply more comprehensive methods of vigilance monitoring. These more comprehensive monitoring techniques can include techniques for analysing the frequency composition of a subjects EEG physiological data. Half Period Amplitude analysis (AU patent 632932) or spectral analysis can be applied in order to determine if the subject is entering a trance or non-vigilant state or if the subject is becoming drowsy. This type of sleep staging can be derived in real time to facilitate determination of the subject's state of vigilance. If the subject is detected as being in a risk category the present system will alert the driver in order to prevent a potential vehicle accident due to the driver's lapse in concentration.

One method of electrode attachment, but not limited to, could be the application of a headband by the driver where this head-band and/or chin-band could connect the EEG, EMG and EOG signals to the monitoring device for purpose of analysing the signals for determination of the subjects state of wakefulness.

6. Driver Eye Sensor

Various techniques can be applied for the purpose of eye movement monitoring including;

Techniques based on reflected light.
Techniques based on electric skin potential.

Techniques based on Contact lenses
Techniques based on Limbus tracking
Techniques based on video imaging
Techniques based on Magnetic Induction
Driving goggles or glasses with infra-red detection capability for monitoring driver's eye movements, or EOG signal pick up via electrodes.

Driver Eye Detection Sensor Types;
   Driver's eyes left
   Driver's eyes right
   sources of eye movements can include EOG electrodes, Infrared detection of eye movements, or video tracking and processing of eye movements.

7. Driver Steering Wheel Sensor

The driver steering wheel or other steering device sensors can be, for example, a CSDM or PVD material that can be divided into the various sections (as listed below) of the driver's steering wheel or other steering device. The output from the various sensors is amplified, filtered, and finally data acquisitioned and analysed.

Figure 6:
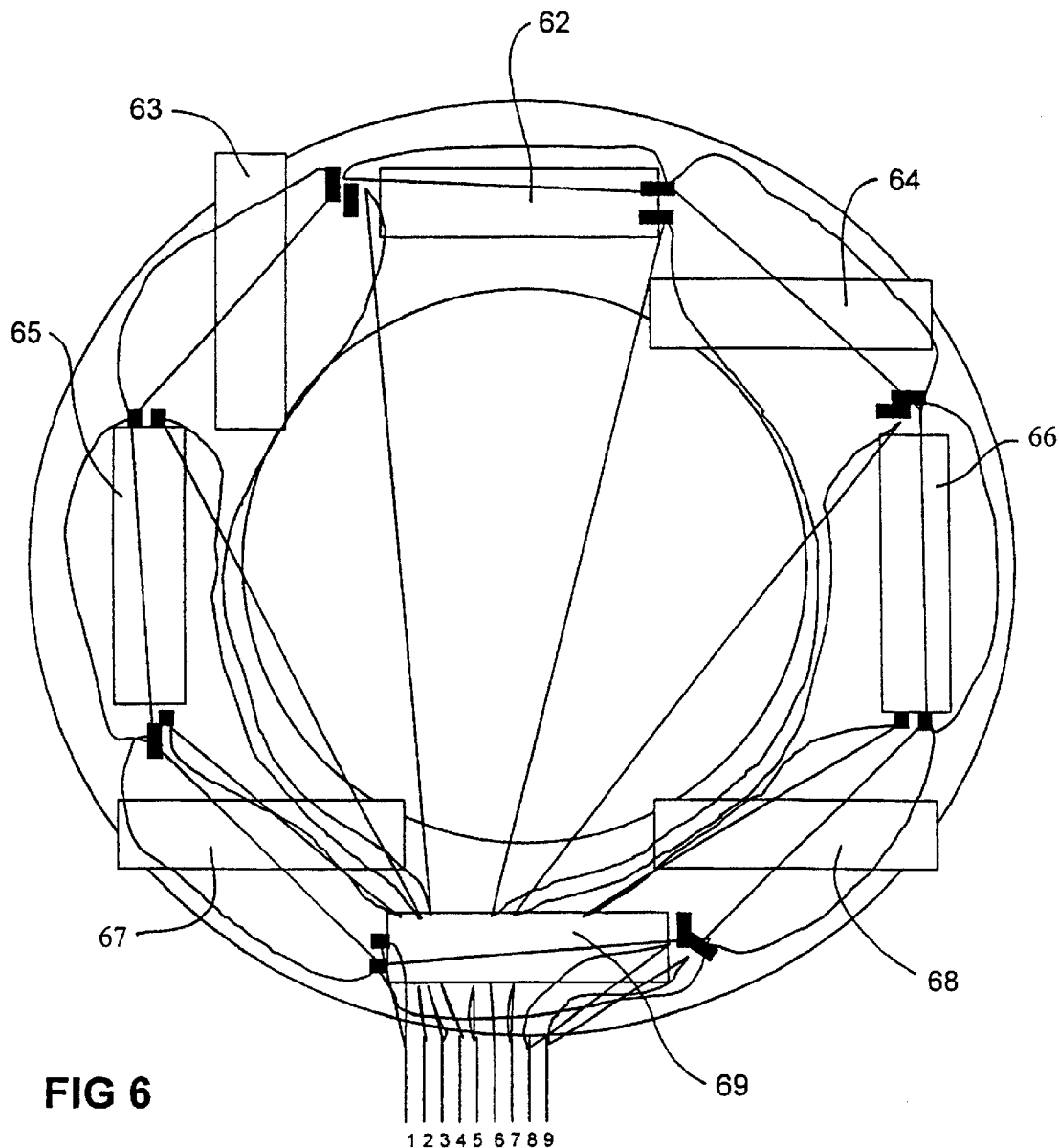
FIG. 6 shows an embodiment of steering wheels sensors.

Driver Steering Wheel Sensor Types;
   Drivers steering wheel top left section
   Drivers steering wheel top right section
   Drivers steering wheel bottom left section
   Drivers steering wheel bottom right section An alternative form of steering wheel sensor is shown in FIG. 6.

8. Driver Carpet Region Sensor

The driver carpet sensors can be, for example, a Capacitive Static Discharge Material (CSDM) or PVD Material (PVDM) that can be divided into the various sections (as listed below) of the driver's carpet area. The output from the various sensors is amplified, filtered and finally data acquisitioned and analysed.

9. Driver Accelerator Sensor

The driver accelerator sensors can be, for example, a Capacitive Static Discharge Material (CSDM) or PVD Material (PVDM) that can be divided into the various sections (as listed below) of the accelerator pedal. The output from the various sensors is amplified, filtered and finally data acquisitioned and analysed.

Driver Accelerator Pedal Sensor Types;
   Drivers accelerator pedal top section
   Drivers accelerator pedal center section
   Drivers accelerator pedal bottom section

10. Driver Clutch Pedal (Where Applicable) Sensor

The driver clutch sensors can be, for example, a Capacitive Static Discharge Material (CSDM) or PVD Material (PVDM) that can be divided into the various sections (as listed below) of the driver's clutch pedal (where applicable). The output from the various sensors is amplified, filtered and finally data acquisitioned and analysed.

Driver Clutch Pedal Sensor Types;
   Drivers clutch pedal (if applicable) top section;
   Drivers clutch pedal (if applicable) center section
   Drivers clutch pedal (if applicable) bottom section

11. Driver Brake Pedal Sensor

The driver brake sensors can be, for example, a Capacitive Static Discharge Material (CSDM) or PVD Material (PVDM) that can be divided into the various sections (as listed below) of the brake pedal. The output from the various sensors is amplified, filtered and finally data acquisitioned and analysed.

Brake Pedal Sensor Types;
   Drivers Brake Pedal Top Section
   Drivers brake pedal center section
   Drivers brake pedal bottom section Other sensors are referred to in block 13, including steering wheel movement and direction sensors and sensors for detecting environmental noise and vibrations.

The outputs from the various sensors are amplified and filtered in block 14 in preparation for analog to digital conversion in block 15. The sensor signals are input in digital form to block 16. Block 16 includes a central processing unit and one or more algorithms for processing the digital signals. Block 16 also makes use of the vigilance processing algorithm(s) in block 17. The vigilance processing algorithm(s) in block 17 are adapted to determine the status of the driver state of vigilance, alertness or wakefulness. This status may be expressed as a vigilance factor (0–100%). Upon detecting a vigilance factor which is below an acceptable threshold, the central processing unit may alert the driver of the vehicle and/or other vehicles. The driver alert means may include:
   To alert external drivers;
   Flashing Hazard Lights
   Sounding of siren
   Internal vehicle driver alert systems;
   Scent sprays which are designed to activate the drivers vigilance state
   Vibration modulation for driver can include vibration of steering wheel or floor area to alert driver
   Vibration modulation for driver seat-belt
   Vibration modulation for driver steering wheel
   Audible alarm system at frequencies and durations or sequence of durations as tested be most effective in alerting the driver
   Cabin bright lights designed to avoid driving hazard but tested for improving driver vigilance Upon detecting a vigilance factor which is below an acceptable threshold, the central processing unit may intervene in the control of the vehicle. Vehicle intervention may enable the vehicle to be brought into a safe or safer status. Vehicle intervention may include speed restriction or reduction or complete removal of fuel supply. In some circumstances the accelerator pedal may need to be disabled, for example when a driver has his foot depressed on the accelerator pedal and is in an unsafe or fatigued state.

Where a driver is detected as ignoring or not responding to response requests or appropriate acknowledgement that the driver is in a vigilant state, the vehicle may have its horn or hazard flashing lights activated to warn other drivers, and/or have its fuel injection de-activated, and/or speed reduced by gentle and controlled safe braking.

Where a driver is detected as suffering from fatigue and is not responding to response tests, the vehicle may have its fuel supply reduced, and/or its speed reduced by gentle and controlled safe braking, to a safe cruising speed. The driver may then be prompted again before the vehicle undergoes further intervention.

Another option for vehicle intervention is to provide a form of ignition override, as used in some alcohol based systems. In this type of system the vehicle ignition or starting process may be inhibited by an inappropriate driver state which in the present case may be drowsiness or excessive fatigue.

In many modern vehicles vehicle intervention options may be instigated by an onboard computer or electronic interface eg. by communication with the speed controller or fuel injection logic. The computer system, may include intelligence to arbitrate the most appropriate intervention sequence or process to minimize risk to the vehicle driver or its passengers.

Figure 2:
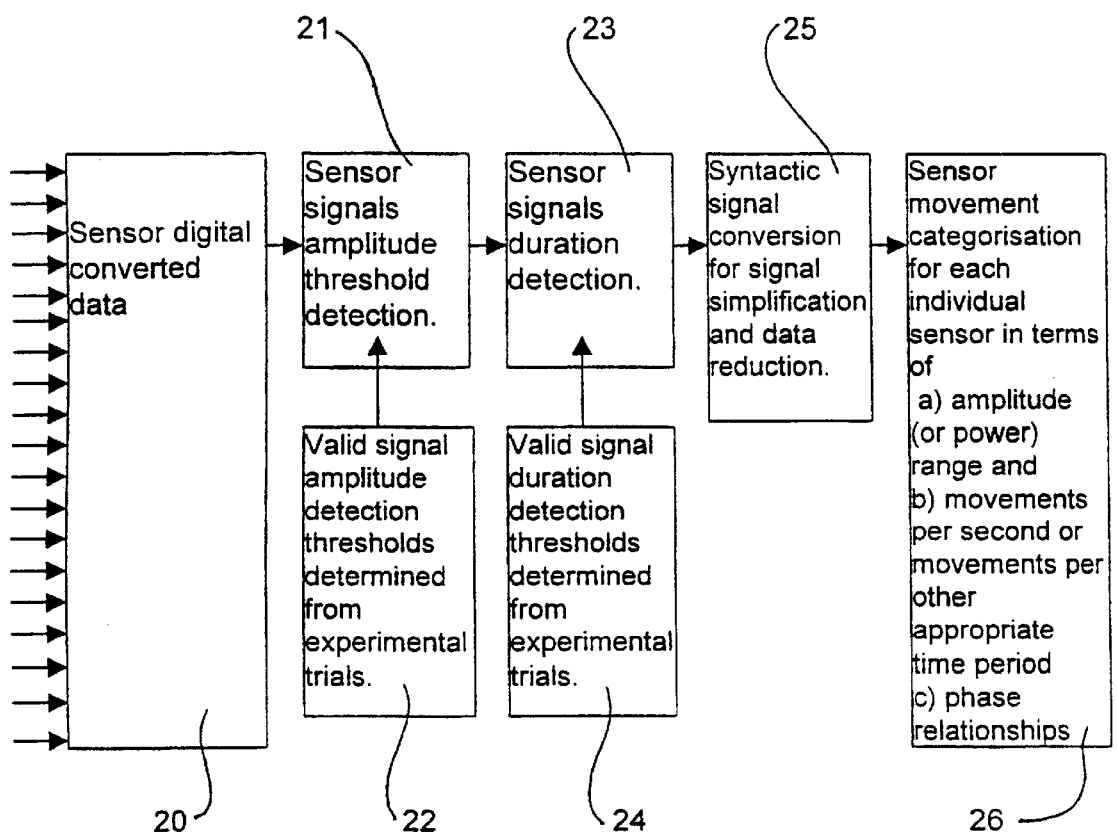
FIG. 2 shows a flow diagram of an algorithm for processing data from sensors associated with a vehicle and driver.

FIG. 2 shows a flow diagram of an algorithm for processing data from sensors associated with the vehicle and driver. Block 20 shows a plurality of arrows on the left representing data inputs from various sensors associated with a vehicle, following conversion to digital data. The digital data is input to block 21 which determines whether the data conforms to valid amplitude thresholds stored in block 22. Signals beyond the thresholds are classified as noise or artefact and are ignored. The data is then input to block 23 which detects whether the data conforms to valid time duration thresholds stored in block 24. Signals beyond the thresholds are classified as invalid and are ignored. The thresholds stored in blocks 22 and 24 are, for the purpose of the present embodiment, determined empirically from experimental trials. The data is then input to block 25 for signal compression. The role of block 25 is to simplify further processing by presenting the data in a minimized form. This is done by syntactic processing whereby main data points only of the signals such as various peaks, troughs and zero crossings or central points defining peaks of the signals are presented for further processing. The data is then input to block 26 where it is categorized and summarized in terms of amplitude or power range, number of movements per second or other epoch, and phase relationships between the signals. The data may be displayed on tabular or graphical form and/or may be subjected to further automated processing to determine vigilance status.

Figure 3A:
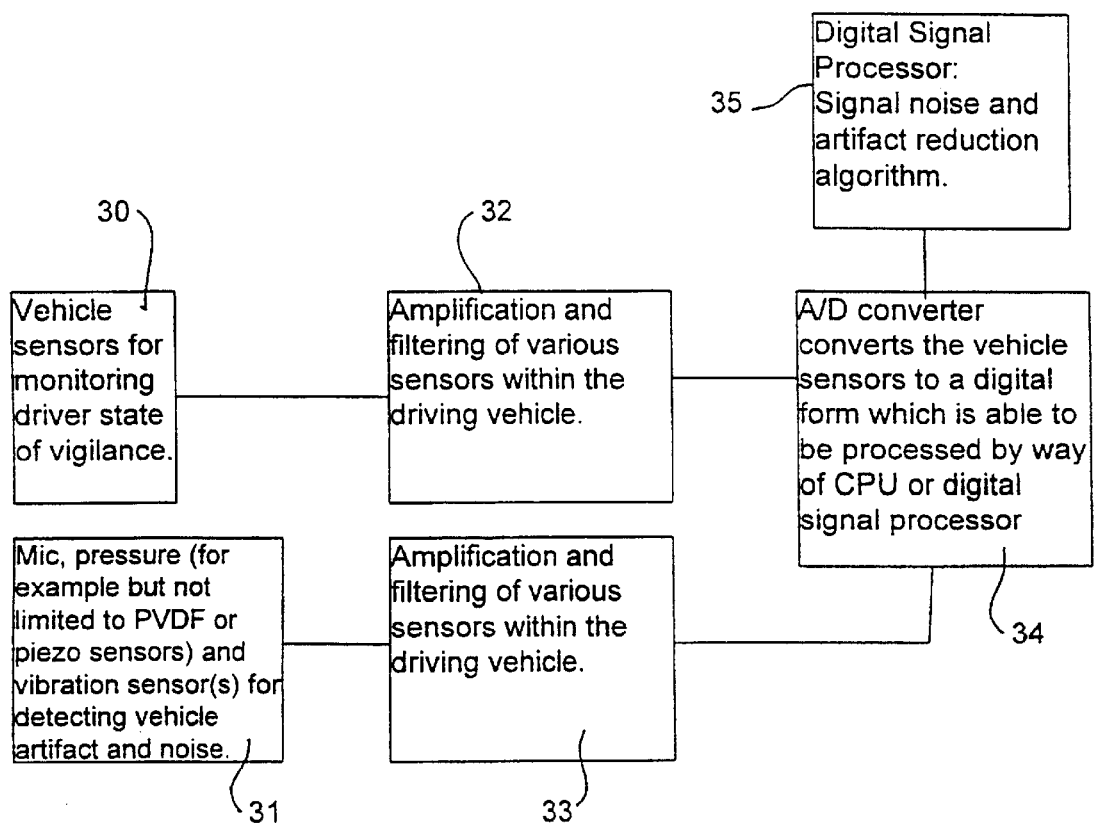
FIG. 3A shows a simplified block diagram of a system for cancelling environmental noise from driver interfaced sensors.

FIG. 3A shows a block diagram of a system for removing environmental noise from driver interfaced sensors. Block 30 represents various sensors for monitoring driver movements and block 31 represents sensors for monitoring environmental vibration and noise and vehicle artefacts.

Blocks 32 and 33 represent circuits for amplifying and filtering signals from blocks 30 and 31 respectively. Block 34 represents analogue to digital converters for converting the signals from blocks 32 and 33 into digital form for processing via the digital signal processor in block 35. Block 35 includes an algorithm for performing signal cancellation as illustrated in FIG. 3B.

Figure 3B:
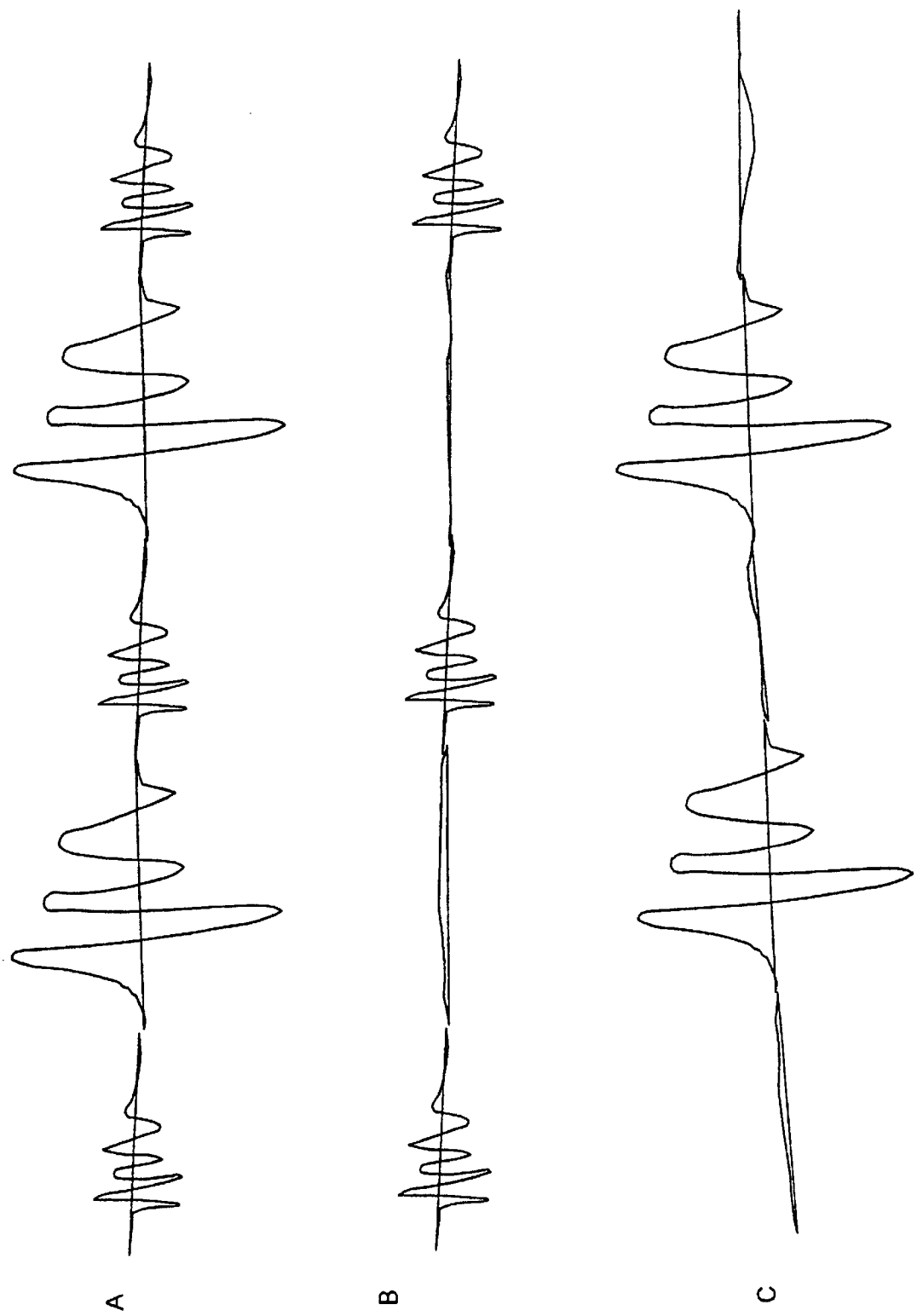
FIG. 3B shows waveforms associated with the system of FIG. 3A.

In FIG. 3B waveform A represents a signal from a driver interfaced sensor or sensors (Block 30 of FIG. 3A). Waveform B represents a signal from a sensor or sensors associated with the vehicle engine and road noise pickup locations (Block 31 of FIG. 3A). Waveform C represents a signal after it is processed by Block 35. It may be seen that the signal represented by waveform C is obtained by cancelling or subtracting the signal represented by waveform B from the signal represented by waveform A. The signal represented by waveform C is a true or valid movement signal which is not corrupted by environmental noise.

Figure 4A:
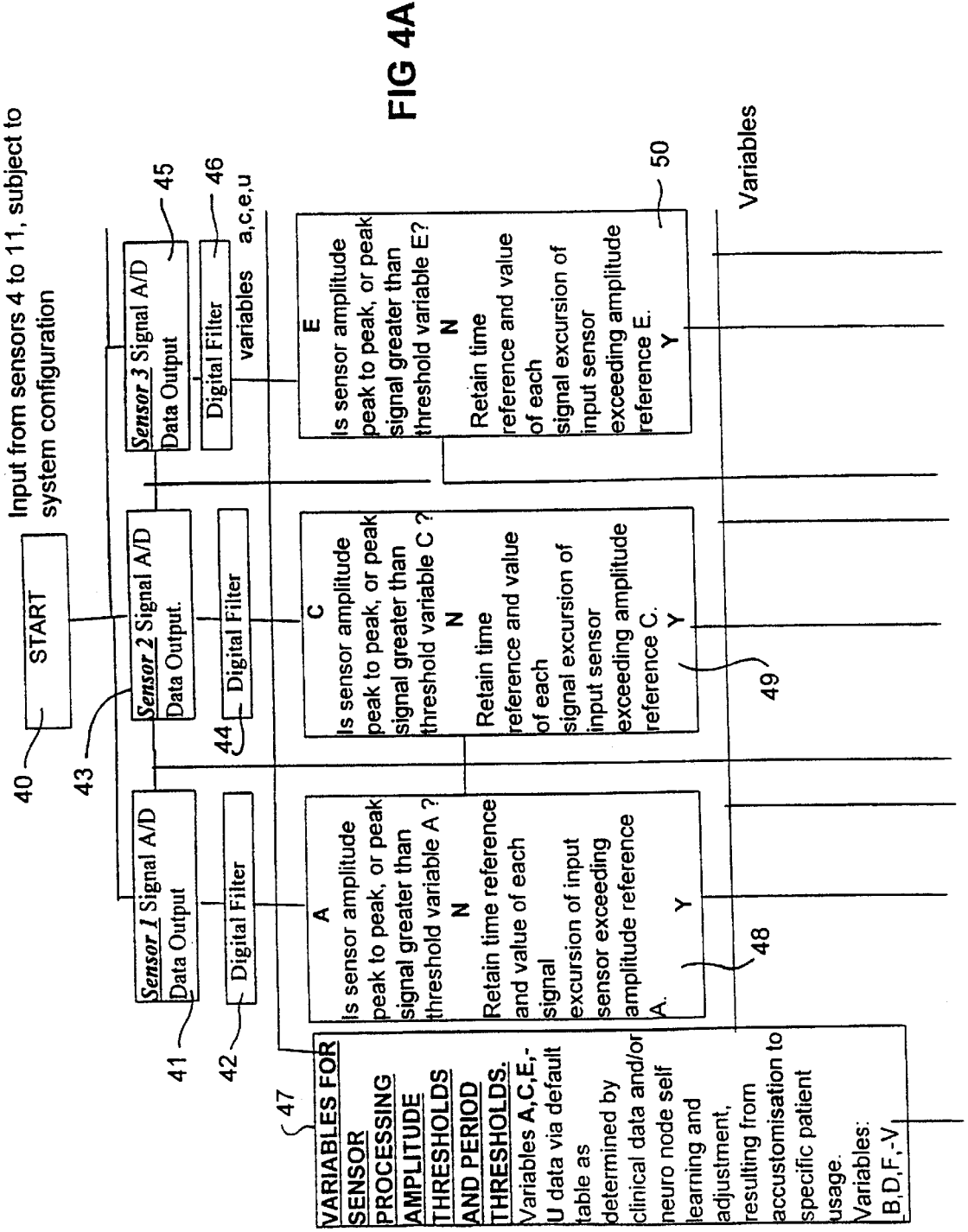
FIG. 4A shows a flow diagram of a movement processing algorithm according to the present invention.
Figure 4A:
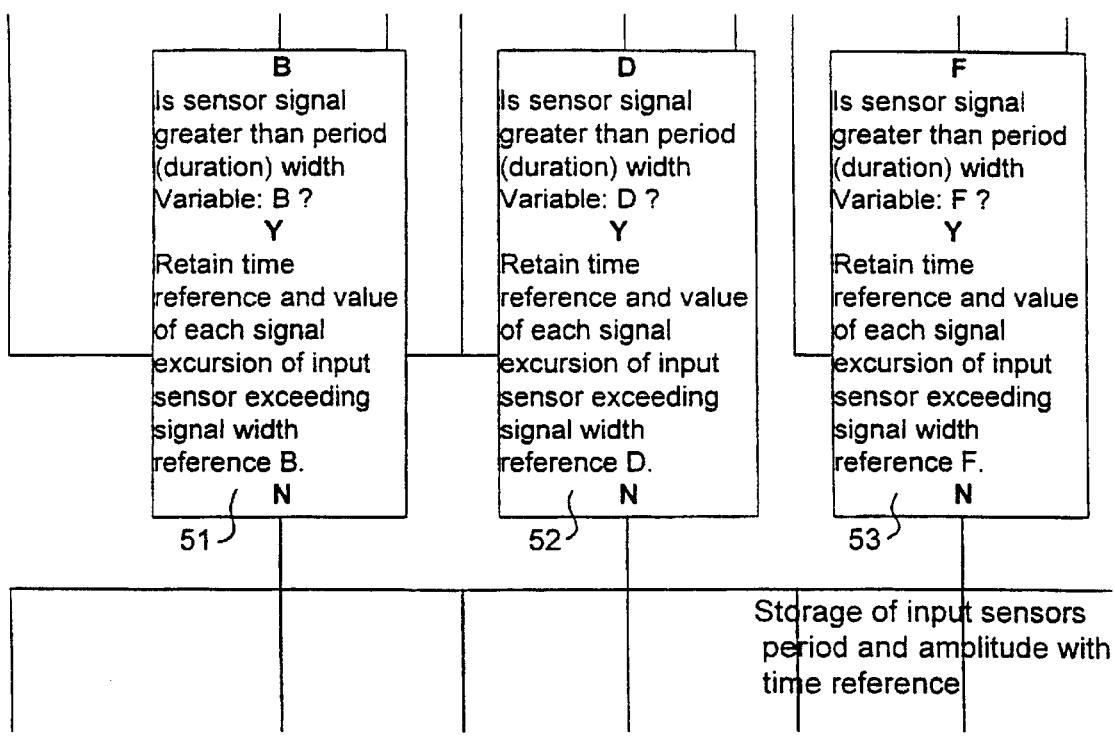

FIG. 4A shows a flow diagram of a movement processing algorithm according to the present invention. Referring to FIG. 4A, signals from sensors 1 to 11 shown in block 12 of FIG. 1 are filtered, then referenced to period and amplitude threshold values before being converted to syntactic data. The syntactic data is correlated for determination of certain combinations of sensor movement signals indicating that the driver is in a vigilant or wakeful state. When a sensor signal or any combination of sensor signals are analysed as being void of subject movement, this may be interpreted as an indication the driver is suspected of being in a non-vigilant or fatigued state. Analysis of the fatigued state is determined by certain expected patterns from the various sensor signals. Such patterns include very little movement from the steering wheel and very little movement from the seat sensors, indicating that the driver may be excessively relaxed and subject to fatigue, or at risk of fatigue on-set. The functions of blocks 40 to 61 are as follows:

Block 40

FIG. 1 shows how the analog signals from sensors 1 to 11 are: converted to a digital signal (FIG. 1, block 15); input to the central processing unit (FIG. 1, block 16); and processed by a vigilance processing algorithm (FIG. 1+block 17). The start of the algorithm in FIG. 4A represents the start of a process, which is repeated many times for each input sensor 1 to 11 (FIG. 4A shows the process for sensors 1, 2, 3). This process analyses data from each input sensor for the purpose of final determination of the driver's vigilance state, and whether this state warrants an alarm alert in order to assist in preventing a potential accident.

Blocks 41 to 46

Signal A/D Data Output. The analog signal from each sensor is amplified, filtered and then converted to a digital signal in preparation for signal processing.

Variables A,C,E-U

Figure 4B:
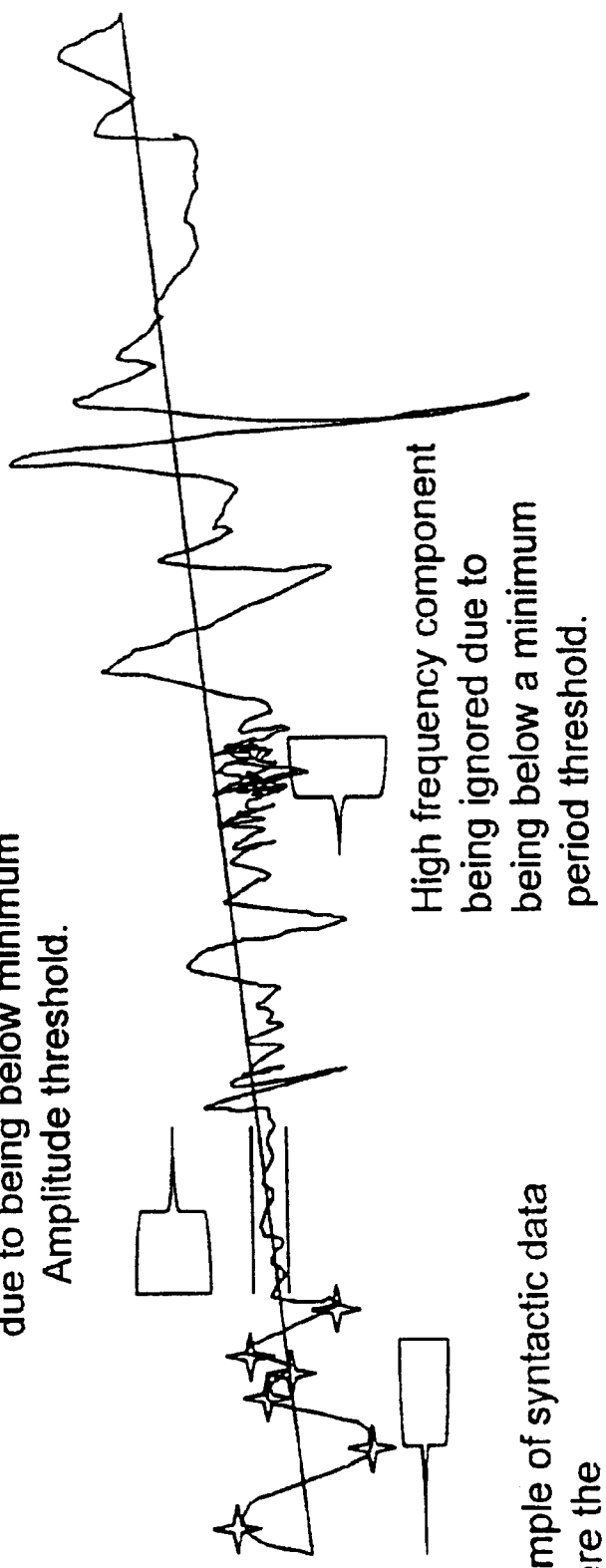
FIG. 4B shows examples of data reduction and syntactic signal processing associated with a sample signal waveform.

Variables A,C,E,-U provide to the processing algorithms threshold amplitude and period values to allow sensor signal data reductions to be determined and to allow data reduction and syntactic signal processing. The variables (A,C,E-U) are determined via controlled studies from experimental and research data. FIG. 4B shows examples of: (1) signals components which are ignored due to being below a minimum amplitude threshold, (2) syntactic data where the signal is represented by troughs and peaks of the signal, and (3) high frequency component being ignored due to being below a minimum period threshold. The latter recognizes relatively lower frequencies which are typically due to driver movements.

Inputs from Sensors 4 to 11, Subject to System Configuration

Input from each of the vehicles sensors is amplified, filtered and then analog to digital converted, in preparation for signal processing. This is performed by blocks similar to blocks 41 to 46. Inputs from more than 11 sensors can be catered for if required.

Block 47

A,C,E,-U

Variable data via default table (as determined by clinical data and/or neuro node self learning and adjustment), resulting from customisation to specific subject's driving characteristics and system adaptation.

Variables: B,D,F,-V . By comparing the sensor data to various amplitude thresholds and pulse periods, it is possible to ignore data that is likely to be noise or artefact and include data that is distinguishable as movement data from a driver. The movement data is distinguished by measuring the amplitude and period characteristics of the sensor signal. Movement data is also distinguished by comparing signal patterns and characteristics of sensors to patterns and characteristics of typical driver's movements (as determined by comparative data used for correlating against current data, this data being derived from system self-learning and/or calibration processes.)

Block 48

Is peak to peak amplitude of sensor output greater than threshold variable A? Retain time reference and value of each signal excursion of input sensor exceeding amplitude reference A.

Block 49

Is peak to peak amplitude of sensor output greater than threshold variable C? Retain time reference and value of each signal excursion of input sensor exceeding amplitude reference C.

Block 50

Is peak to peak amplitude of sensor output greater than threshold variable E? Retain time reference and value of each signal excursion of input sensor exceeding amplitude reference E.

Block 51

Is peak to peak amplitude of sensor output greater than threshold variable B? Retain time reference and value of each signal excursion of input sensor exceeding amplitude reference B.

Block 52

Is peak to peak amplitude of sensor output greater than threshold variable D? Retain time reference and value of each signal excursion of input sensor exceeding amplitude reference D.

Block 53

Is peak to peak amplitude of sensor output greater than threshold variable F? Retain time reference and value of each signal excursion of input sensor exceeding amplitude reference F.

Storage of Input Sensors Period and Amplitude with Time Reference

The syntactic data from the full range of sensors is stored in random access memory for the purpose of processing and determination of a subject's vigilant state. The syntactic data is also archived to allow post analysis report and validation or review of driver fatigue and performance. This can be particularly useful where truck drivers and other critical transport or passenger drivers are required to be checked for performance and vigilance compliance.

Block 54

Longer-term data storage is designed to log the driver's movement data from each of the sensors. This stored data can be accessed at a later stage in order to review the driver's performance history in regards to movement analysis and subsequent vigilance.

Block 55

Short term direct access storage used for storing parameters such as the past 10 minutes of syntactic data for each sensor channel, in order to correlate the various data from each sensor or channel and compare this data combination to pre-defined sets of rules designed to describe combinations of sensor outputs which are typical of driver fatigue conditions.

Block 56

Store syntactic representation of sensor signal exceeding threshold A and B, with timer reference, amplitude and pulse width.

Block 57

Store syntactic representation of sensor signal exceeding threshold C and D, with timer reference, amplitude and pulse width.

Block 58

Store syntactic representation of sensor signal exceeding threshold E and F, with timer reference, amplitude and pulse width.

Block 59

Driver specific profile and calibration data can be stored for later correlation reference. By correlating with various thresholds or reference conditions the system is able to determine interaction to sensors when a particular driver's conditions is similar to pre-stored reference characteristics. This comparative data is stored as data in look up tables. The data can consist of frequency and/or amplitude characteristics for a range of driver states or alternatively the data can consist of samples of data (with acceptable variations to the samples of data) that exist for a range of driver states.

Block 60

Vehicle output signals. These include steering wheel movements, direction of steering wheel movements, speed of vehicle, change of speed of vehicle, engine vibration and noise, road vibration and noise.

By processing driver steering wheel adjustments and comparing these adjustments with the various sensor signals and correlation of various sensor signals, it is possible to determine the probability that the driver is in a state of fatigue and the degree of driver fatigue. The vehicle signals are also analysed in order to assist in noise cancellation (ie vehicle noise as opposed to driver movement) and more accurate identification of valid driver movements).

Block 61

Correlate all channels of sensor activity and determine if driver fatigue is a probability and what level of driver fatigue is detected. Look up table of specific driver calibration values and reference states is used to determine actual driver state level of fatigue of driver, along with probability of data accuracy. Standard reference data tables and default values are also used for determination of driver fatigue. See sample R&K style histograms, movement histograms and tables showing weighted value of each sensor and actual movement detection from each sensor to determine fatigue probability as a function of movement detection with appropriate weighting.

FIG. 5 shows typical samples of processed data following secondary analysis for sensor signals 1 to 4. The data shows in graphical form the number of valid movements detected for each sensors 1 to 4 during successive time intervals n, n+1, n+2 . . . . Tertiary analysis may be performed on this data which would allow simple to view correlation between the various sensors. The samples shown in FIG. 5 demonstrate an example (dotted line) where the various sensors all experience obvious movement detection.

The steering wheel sensors shown in FIG. 6 are divided into eight sections as follows:

Top 62, top left 63, top right 64, left 65, right 66, bottom left 67, bottom right 68 and bottom 69.

Sensors 62–69 are linked via eight cables to output pins 1 to 8 respectively. A common connection to each sensor is linked by cables to output pin 9. Alternative configurations are possible with more or less sensors and with the option of sensor arrays on both the upper and lower surfaces of the steering wheel grip surface. The outputs represented by pins 1 to 9 are connected to analogue signal conditioning circuits and via analogue to digital convertors to digital signal processing circuits as described above.

It is desirable to measure pressure of a driver's hand or hands on the steering wheel at all times. The pressure may be compared to previous values and/or calibrated values to determine whether a pattern of increased or decreased pressure reflects driver fatigue onset.

If the driver's state of consciousness or concentration changes due to fatigue onset or the like, the system may calculate and deduce an appropriate point at which the driver should be alerted. The appropriate point may be determined from a combination of pre-calibrated data for a specific driver and/or pre-programmed patterns, states or trends in the data including relative and absolute pressure values obtained from a set or subset of vehicle sensors.

Figure 7:
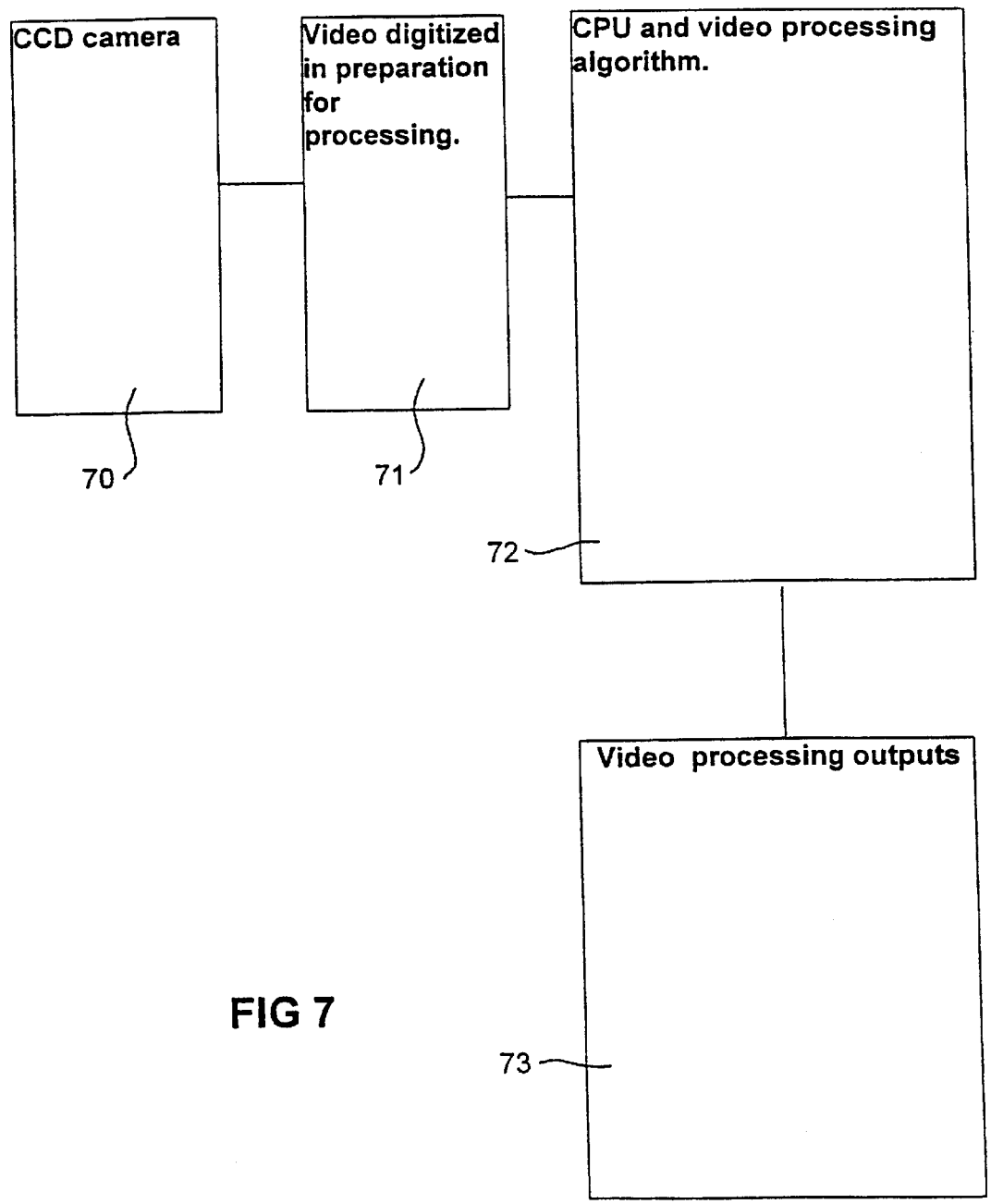
FIG. 7 shows a block diagram of a vigilance monitoring system utilizing video data.

FIG. 7 shows a block diagram of a vigilance monitoring system utilizing video data. Block 70 represents a video CCD (charge coupled device) camera which may be located on the driver's visor, dash-board or other suitable location to enable video monitoring of the driver's eyes. An infra-red lens may be utilized to facilitate reliable night video monitoring capability. The output of the video camera is passed to block 71. Block 71 is an analog to digital converter for digitizing the video signal prior to processing via block 72. Block 72 is a central processing unit and includes a video processing algorithm. The video processing algorithm has eye recognition software designed to identify eyes in contrast to other parts of the drivers face. Eyes are detected using special processing software that allows the driver's eyes to be analysed. This analysis includes determining the area of the eye's opening and correlating the eye's opening area to previous similar measurements. In this way eye processing can determine whether a driver's eyes are remaining open as would be expected in an alert state or whether the current eye opening of the driver is relatively less (when compared to earlier eye opening measurements). Rates or degrees of eye closure are able to be detected and continually monitored in this manner.

The video processing algorithm also detects blink rate and possibly eye movements to determine whether the drivers eyes appear to be alert or possibly fixed in a dangerous "trance state" as may be apparent during lapses of driver vigilance. Block 73 represents outputs of block 72 including eyes blink rate eyes closure, calculated as a percentage ratio of current eyes open area to previously calculated maximal eyes open area.

eyes focus factor, determined by measuring number of eye movements per second, extent of eye movements (ie small eye movements or larger eye movement deflections)

the nature of eye movements can reflect appropriate patterns of movement of a driver's eyes such as focus on sections of the road for an appropriate time as well as inappropriate patterns of movement associated with fatigue or lack of vigilance type of eye movements, ie vertical, horizontal, stare The above measures may be gauged against actual trials in order to determine relevant indices that correlate to a driver's fatigued state.

Figure 8:
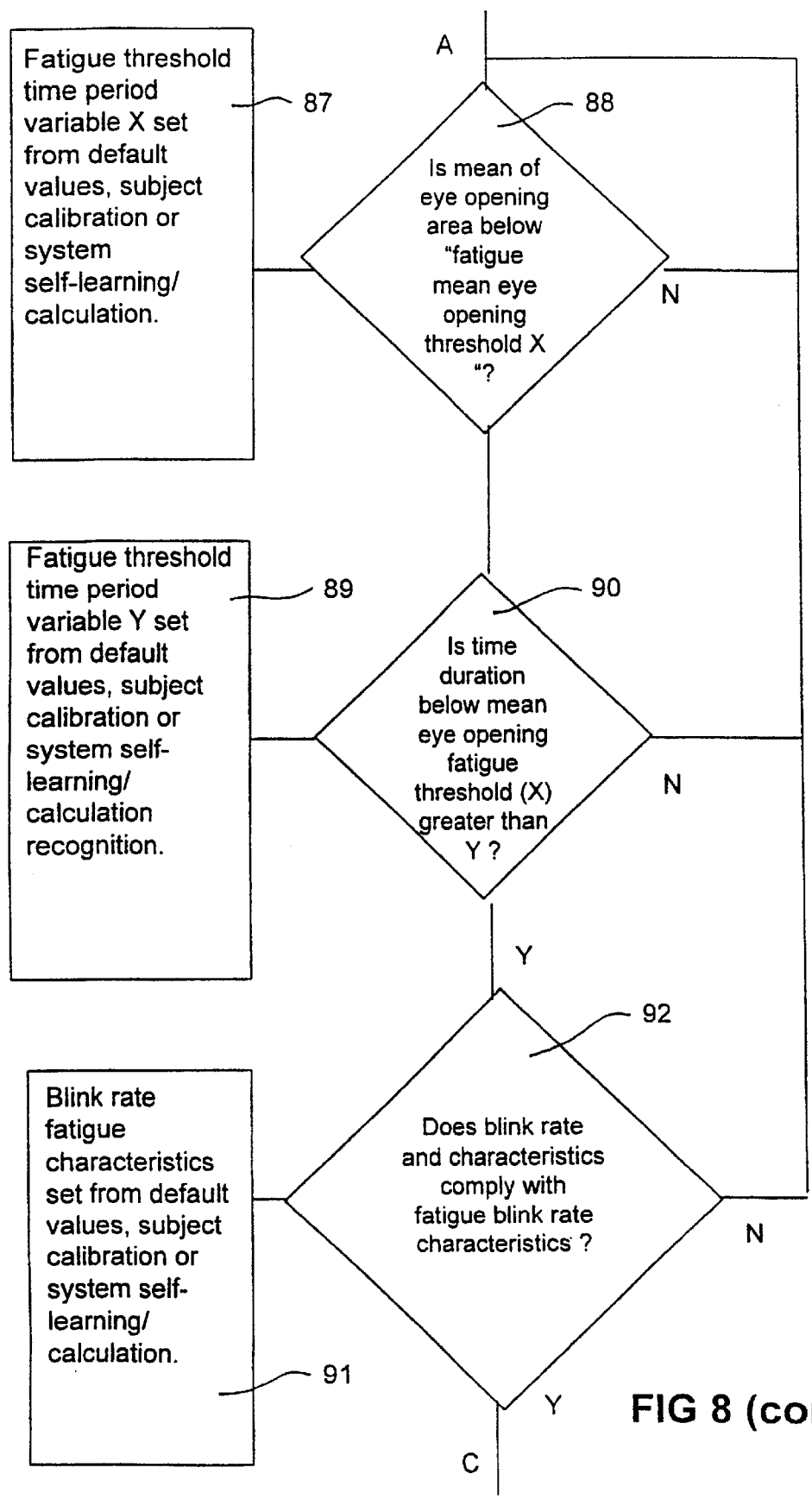
FIG. 8 shows a flow diagram of an algorithm suitable for processing video data.

FIG. 8 shows a flow diagram of an algorithm suitable for processing video data. The functions of blocks 80 to 94 are as follows:

Block 80

Start

Block 81

CAPTURE EYE VIDEO DATA—Capture current video frame. Digitise video frame of subject's eyes. Eye data can be captured via one or more of the following means:

CCD video camera, Electro-oculogram data capture means via subject worn headband, direct electrode attachment, driver glasses, head-cap or movement sensors, infrared or other light beam detection means.

Block 82

Apply Eye Data Processing and Determine Left & Right Eye Opening Area and Blink Events.

Apply edge detection, signal contrast variation and shape recognition, amongst other processing techniques to determine the border of the subject's eye lids. Determine area of each of the subject's eye openings, height of each eye opening, blink events for each eye, blink rate and time reference associated with each blink event.

Block 83

Correlate Current and Past Video Captured Eye Movement Data

Correlate current eye position data with previous position eye data. Review eye position trend data and determine trends and patterns of eye movements that indicate on-set of or driver fatigue state. Patterns include:

states of staring or trance like states indicating loss of road concentration.

slowly rolling eye movements (typical of sleep onset).

eye focus directions and association of these directions with driver fatigue

Process digitised video frame and detect subject's left and right eye movement patterns and activity of eyes and association of this activity with driver fatigue.

Compare current blink rates, past blink rates and look-up table blink rate characteristics, thresholds for various fatigue on-set and fatigue blink rates and blink characteristics associated with various driver states.

Compare current eye opening area with thresholds for fatigue and fatigue on-set conditions to determine vigilant driver eye opening status versus fatigued driver eye opening status.

Block 84

Look up table with characteristic patterns of;

eye movements and threshold data for fatigued versus vigilant subjects.

Blink rate typical thresholds and characteristics

Eye opening typical and default thresholds

Eye movement typical and default characteristics for driver fatigue on-set.

Block 85

Store subject's left & right eye opening area, eye opening height, blink rates, eye position and eye movements together with time reference.

Block 86

Calibration data derived from subject and vehicle calibration procedures.

determination of fatigue on-set blink rates thresholds.

Determination of eye opening fatigue on-set thresholds.

Determination of eye position, movement characteristics and activity characteristics for fatigue on-set thresholds.

EOG patterns for wake, drive activity, fatigue on-set, fatigue.

Trance and hypnotic EOG eye characteristics.

Block 87

Fatigue threshold time period variable X set from default values, subject calibration or system self-learning/calculation.

Block 88

Is mean of eye opening area below fatigue mean eye opening threshold X"?

Block 89

Fatigue threshold time period variable Y set from default values, subject calibration or system self-learning/calculation.

Block 90

Is time duration below mean eye opening fatigue threshold (X) greater than Y?

Block 91

Blink rate fatigue characteristics set from default values, subject calibration or system self-learning/calculation.

Block 92

Does blink rate and characteristics comply with fatigue blink rate characteristics?

Block 93

Apply eye data processing and determine left & right opening area and blink events.

Correlate current and past video captured eye movement data.

Detection of fatigue eye opening on-set and detection of fatigue blink rate on-set.

Block 94

Eye movement fatigue determination diagram.

FIG. 9 and 10 show examples of eye opening and eye position data produced by the system of FIGS. 7 and 8.

FIG. 11 is a flow chart of the main vigilance processing algorithm. The functions of blocks 95 to 99 are as follows:

Block 95

Main Vigilance Processing Algorithm

Vigilance Movement Processing Algorithm. (see FIG. 4A)

Vigilance Eye Status Processing Algorithm.

Probability of Driver Fatigue and Degree of Vigilance Determination Algorithm (correlates subject Movement Status and Eye Processing Status).

Block 96

LED indicator display panel.

Block 97

Eye Status Vigilance factor 0–100%.

Block 98

Movement Vigilance Factor

0–100%-displayed as bar graph, meter or other means.

Block

Block 99

Vigilance probability Factor 0–100%

Figure 12:
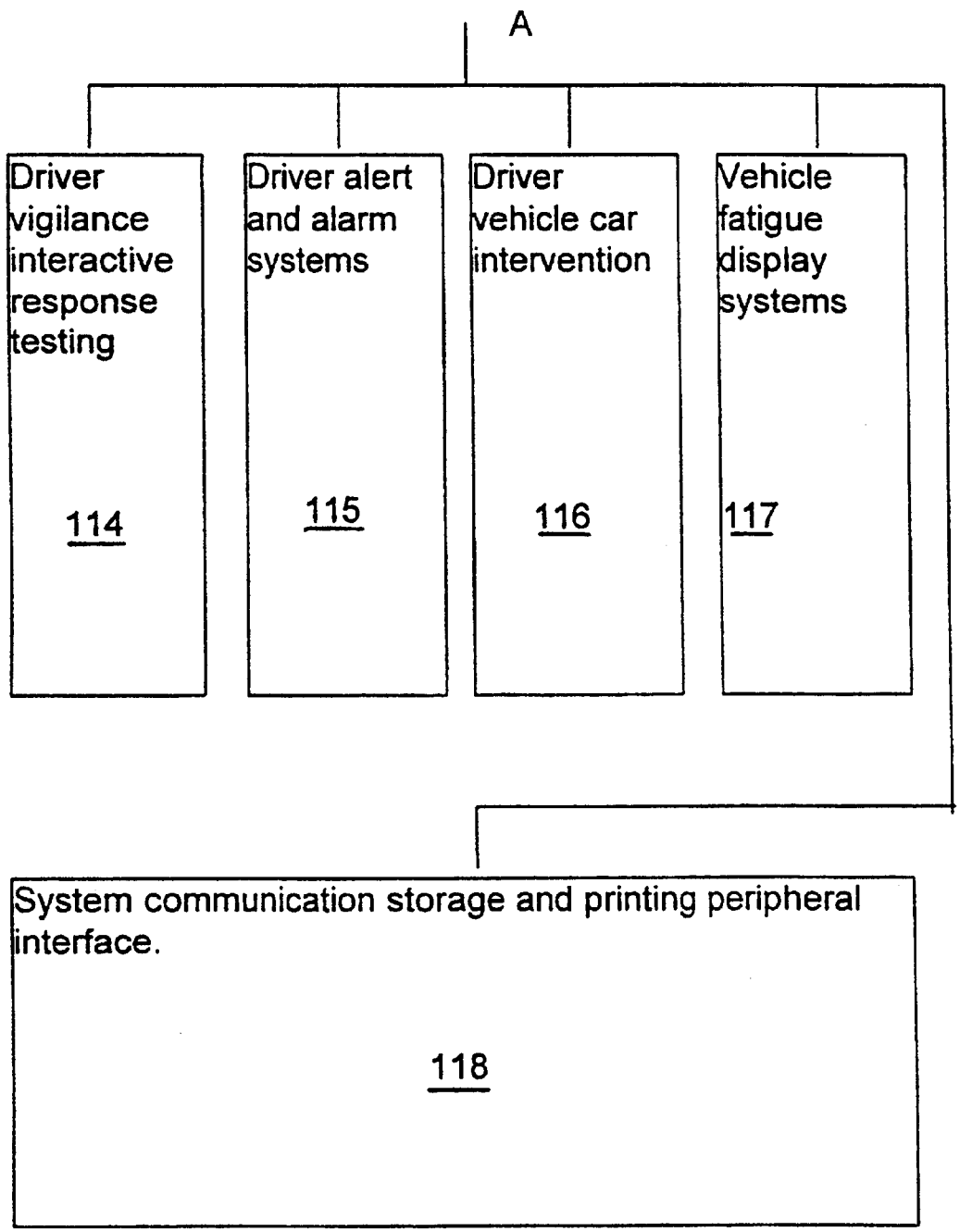
FIG. 12 is a block diagram of a vehicle monitoring system according to the present invention.

FIG. 12 is a block diagram of a vehicle monitoring system according to the present invention. FIG. 12 is an overview of a system which utilizes many of the features discussed herein. The functions of blocks 100 to 118 are as follows:

Block 100

Driver EEG sensors-direct attach electrode, headband, wireless electrode, driver cap and other EEG signal pick-up means.

Block 101

Driver EEG sensors-direct attach electrode, headband, wireless electrode, driver cap and other EEG signal pickup means.

Block 102

Driver Motion, Movement and Physiological Parameter sensors.

Block 103

Driver Eye movement

Detection via electrode, driver glasses/goggles, infrared or other light beam means of tracking detection or other means.

Block 104

Vehicle status interface; speed, direction, accelerator position, break position, indicators, lights amongst other vehicle status data.

Block 105

In phase signal detection and processing. Applies processing which determines patterns of in-phase signal occurrence and associates these with driver or background noise as originating source.

Block 106

Anti-phase signal detection and processing. Applies processing which determines patterns of anti-phase signal occurrence and associates these with driver or background noise as originating source.

Block 107

Vehicle Background Noise Processing Algorithm.

Vehicle background and Environmental Noise Sensors to allow noise cancellation, filtering and reduction.

These sensors include microphone and vibration sensors located at strategic positions in order to pick up background vehicle noise such as road noise and engine noise. Fourier transform and frequency analysis of background noise assists in selection of digital filtering characteristics to most effectively minimise vehicle environmental noise and assist in distinguishing driver related fatigue monitoring signals. System will continually "self-learn" various vehicle background and threshold noise levels, frequency and other characteristics in order to determine changing vehicle noise conditions and subsequent noise cancellation or capability to ignore unwanted vehicle noise while processing "real" driver movement and physiological signals and subsequent fatigue status.

Artificial intelligence;

Signal characteristics as generated by a range of varying road conditions can be programmed into the system. The input data relating to various road conditions thereby provides a means to further distinguish wanted driver related signals from unwanted background noise signals.

Block 108

Driver EEG sensors-direct attach electrode,Algorithm

Block 109

Driver EEG sensors-direct attach electrode, algorithm

Block 110

Driver Motion, Movement, Physiology algorithm

Block 111

Driver Eye Movement Detection Algorithm

Block 112

Vehicle status interface Algorithm

Block 113

Driver Fatigue Processing Algorithm. Correlation with previous driver fatigue conditions together with comparison of outputs for each of above listed fatigue algorithms (Driver EEG, motion, eye, vehicle status).

Block 114

Driver vigilance interactive response testing.

Block 115

Driver alert and alarm systems for re-instatement of vigilance.

Block 116

Driver vehicle car intervention to reduce or limit speed and other means of increasing vehicle safety and reducing vulnerability to driver fatigue status.

Block 117

Vehicle fatigue display systems for displaying to the driver the current fatigue status or early warning indicators of fatigue status.

Block 118

System communication storage and printing peripheral interface. Data storage, reporting processing, reporting print interface, wireless and wire connected interfaces, for real-time or post communication of fatigue data and fatigue status information. System can include GSM, cellular phone, satellite or other means of moving vehicle tracking and data exchange in real-time or at any required later stage. This information transfer can be an effective means for trucks and other vehicles to have their driver status processed and reviewed, as appropriate and as required.

Figure 13:
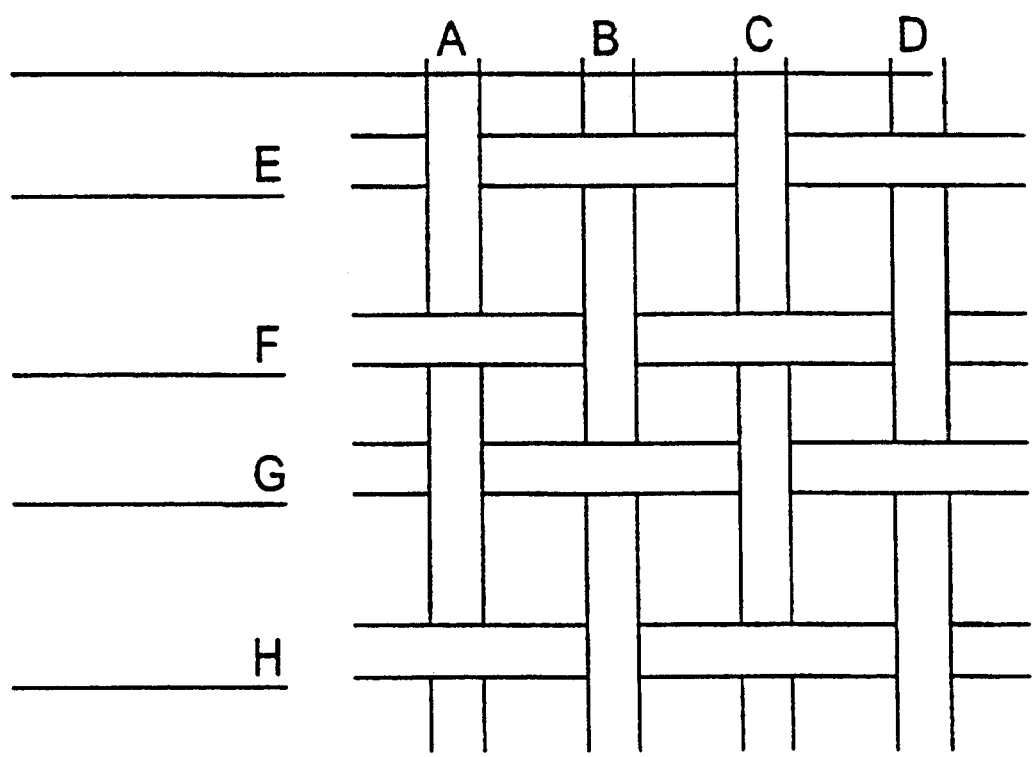
FIG. 13 shows one form of transducer for monitoring posture of a driver or equipment operator.

FIG. 13 shows one form of transducer for monitoring posture of a driver or equipment operator. FIG. 13 shows a webbed structure comprising strips or elements of flexible PVDF or Piezo material separated by flexible insulation material terminated at A, B, C, D, E, F, G and H. Output signals from the respective strips are buffered, amplified, filtered and then analog to digital converted to data. This data may be processed to determine an actual position of pressure applied to the above structure. By analysing the two main co-ordinates and the amplitudes of signals associated with those co-ordinates, the exact position of pressure applied by the vehicle driver or equipment operator may be determined.

The position where greatest pressure is applied is defined by the intersection of web strip pairs (eg. B and F) which produce the greatest signal amplitude. The position may be described by coordinates reflecting the web strip pairs (eg. B,F) which produce the greatest signal amplitude. The above transducer may be used in conjunction with the movement sensors described herein to provide a further layer of positional information relating to applied pressure for each sensor. This information may be important in circumstances where a driver's pressure to the steering wheel or the driver's pattern of hand placement (with respective applied pressure) varies in accordance with alertness and drowsiness.

The posture of the driver or equipment operator may be monitored, stored, correlated with various threshold states and/or displayed in meaningful graphic or numerical form. The threshold states may be derived by way of calibration for each specific driver's posture profile under various states of fatigue and/or stress states and conditions.

Figure 14:
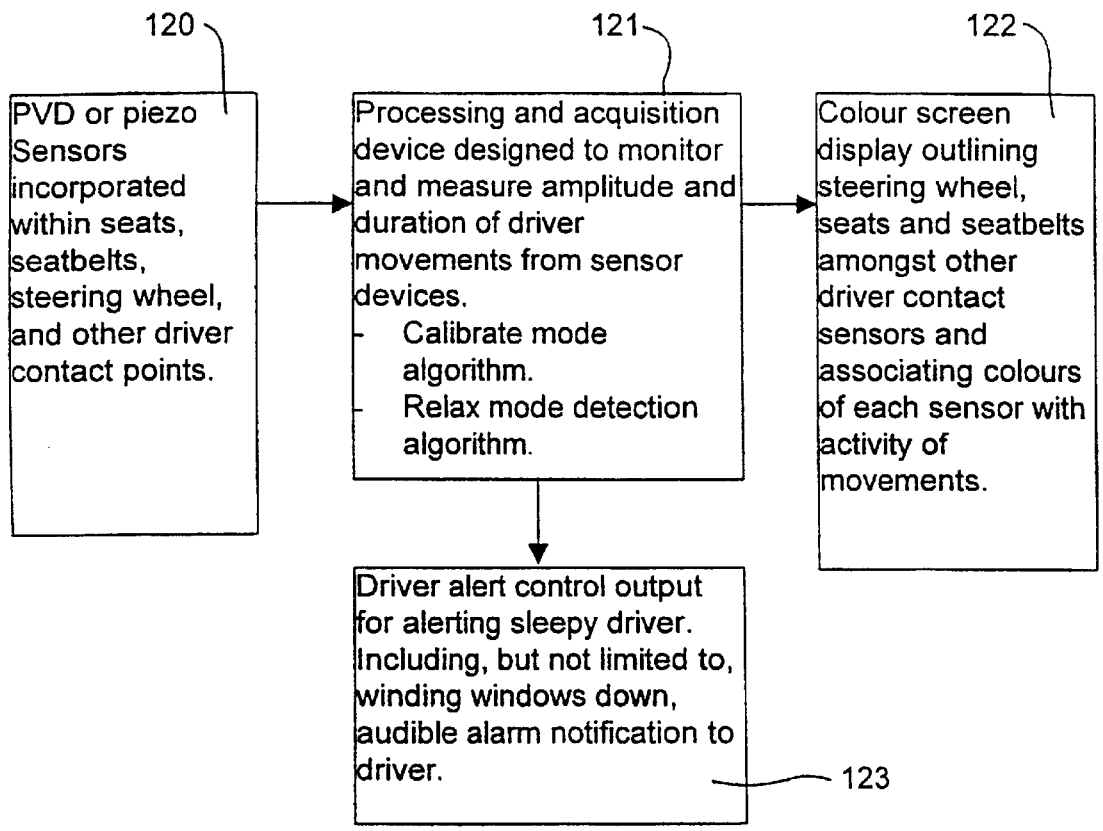
FIG. 14 shows a block diagram of an embodiment of an anti snooze device according to the present invention.
Figure 15:
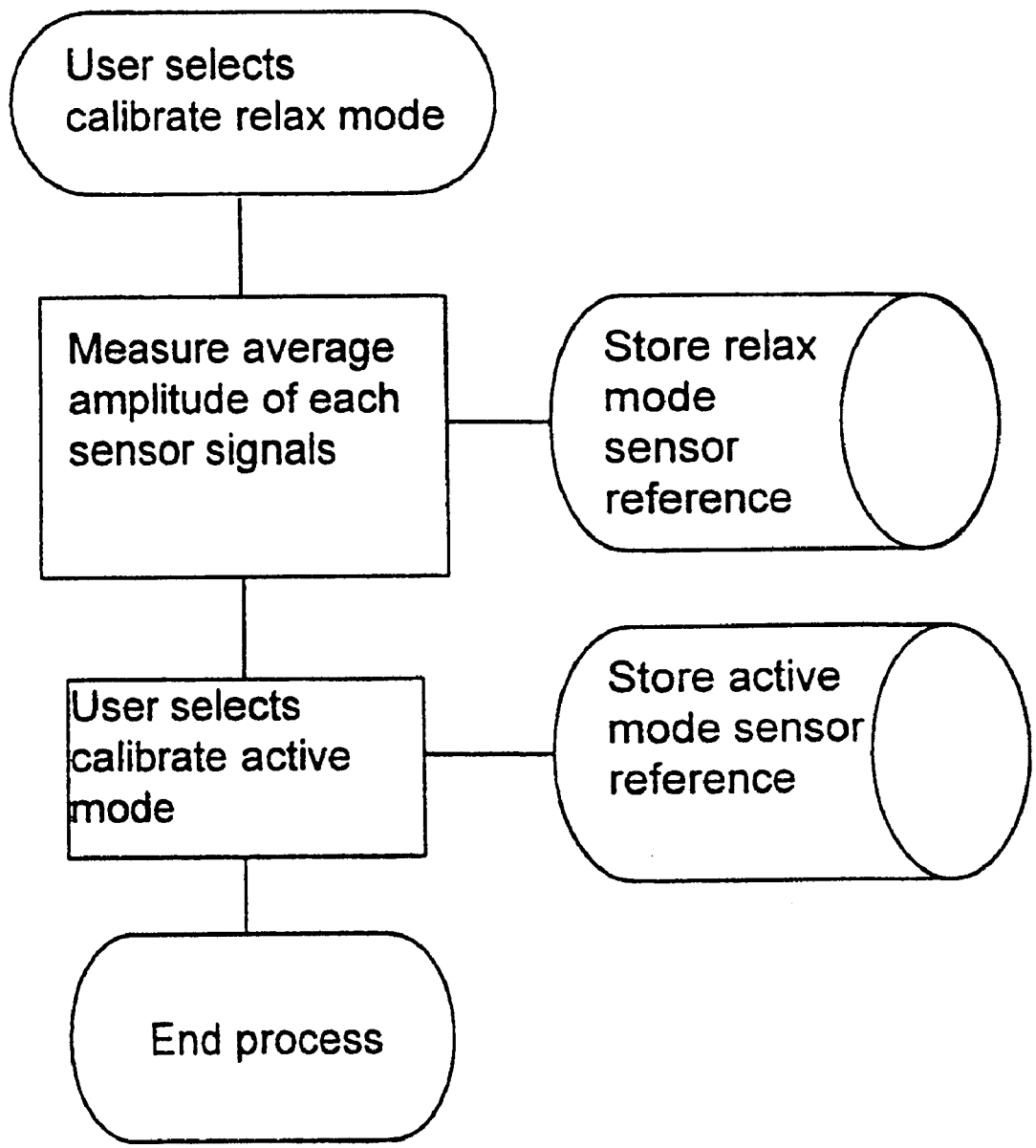
FIG. 15 shows a calibrate mode algorithm.
Figure 16:
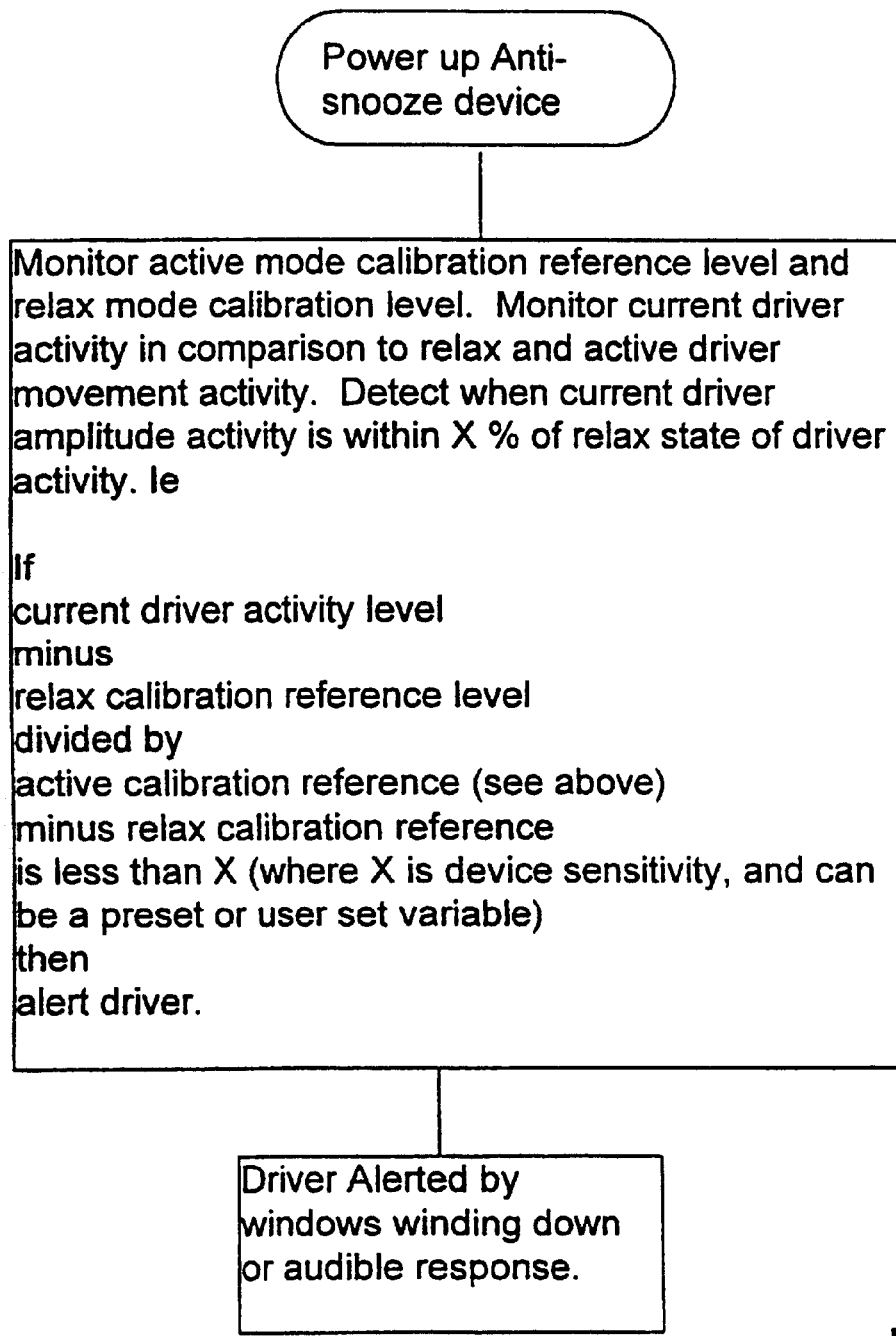
FIG. 16 shows a main relax detection algorithm.

The anti-snooze device shown in FIG. 14 includes sensors (block 120) connected to an acquisition and processing means (block 121). Block 122 includes monitoring means designed to amplify, filter and digital to analog convert driver sensor signals in preparation for digital signal processing. The digital signal processing means (block 121) includes a calibration algorithm as shown in FIG. 15 and a main relax detection algorithm as shown in FIG. 16.

The driver can select the relax calibration function, then take on the driving posture that would most closely represents a relaxed or possibly fatigued driving state and the system will then monitor and store the minimum threshold of driver activity over a period of approximately but not limited to 10 seconds, as a relaxed driver reference level.

The driver can select an active calibration function, then take on the driving posture that would most closely represents normal driving state and the system will then monitor and store the minimum threshold of driver activity over a period of approximately but not limited to 10 seconds, as an active driver reference level.

The relaxed and active driver reference levels stored in the system may be displayed on the visual touch screen display for various sensors. The system may perform a validation function by replaying the drivers relaxed and active reference levels on the touch screen. This allows easy comparison to be made with actual sensor levels when the driver adopts postures representing normal/fatigued states and serves to validate the correctness of the stored reference levels.

The driver can also select a sensitivity function which may determine how close to the relaxed level the driver needs to be before the anti-snooze system alerts the driver. By viewing the anti-snooze device screen the driver can relax or adopt normal vigilant driving posture and adjust sensitivity control so that the anti-snooze device appears to track and detect the drivers relaxed state. The anti-snooze device has the ability to act as a self warning aid by simply alerting the driver when his posture or driving vigilance is deteriorating. If, for example, a driver's steering wheel grip erodes or undergoes fatigue, the anti-snooze system can be calibrated to detect this condition and alert the driver.

It is possible for the driver to have calibration data determined by an off-road simulator that more accurately defines the characteristics of each specific drivers activity variations and physiological variations during dangerously relaxed or fatigued driving conditions. The calibration data can be up-loaded to the anti-snooze device to provide more accurate relaxed and active reference levels. The calibration data may also provide more accurate means of determining the relative effect that each individual sensor has during a drivers transition from active and alert to drowsy and fatigued. The effects of each sensor may be recorded and this data may assist in more accurate anti-snooze detection.

During calibration modes the system may detect the drivers hand pressures via the steering wheel sensors, the drivers respiration and ECG via the seatbelt sensors, and the drivers posture and movement via the seat sensors.

The anti-snooze system may continually monitor and average the signal amplitudes of all sensors, while comparing the current levels of sensor amplitude with the calibrated levels. The system may also compare current movement sensor patterns to reference data. This reference data can represent certain threshold levels calibrated to each individual driver or general reference conditions. The various sensors may be weighted in accordance with their respective importance in determining whether a driver's current state of activity is below the threshold or appropriately close to the relaxed mode calibrated reference level to warrant that the driver be alerted.

If the driver is detected as being within the range of sensor amplitudes and activity to warrant being alerted, the anti-snooze device can restrict the speed of the vehicle or slowly bring the vehicle to a stand still in order to reduce the likelihood of an accident. This ability to restrict the vehicle's speed could be overridden by the driver as is possible in "auto-cruise" devices currently available on many vehicles.

The techniques and methodologies may include relatively complex neurological waveform analysis techniques, video tracking of driver eye motions, sophisticated noise cancellation and simpler driver interactive processes such as sensitizing the steering wheel, seat-belt, gear-stick and other driver cabin regions.

One application for the present invention may include a truck driver vigilance monitoring (TDVM) system. This system may be designed around the "dead-man" handle concept as applied successfully in trains. A variation of this system may provide visual cues and driver vigilance response testing.

The TDVM system may include pre-programmed Light Emitting Diode (LED) displays to be activated in various sequences and at various frequencies and durations. The truck driver can be visually prompted by way of these LEDS to press the steering wheel according to whether the left or right or both LEDS are flashed. The response time and accuracy of the driver's response to the prompts may be measured and relayed back to a remote monitoring control station.

Various drivers will have calibrated "vigilant response times and accuracy levels" which can be compared to actual current response times. Where appropriate, an alarm can be activated, if the response times indicate fatigue onset or a potentially dangerous state.

The sequences and durations can be validated in accordance with clinical trials to provide an effective method of vigilance detection. Sequences and patterns of visual truck cabin prompts can be established to minimize driver conditioning. Frequency of vigilance test prompts can be determined in accordance with requirements as determined via field studies.

Safety considerations to avoid driver distraction by the proposed monitoring system may be implemented. Techniques such as utilization of "busy" response prompts especially designed within the system to alert the monitoring control unit that the driver is vigilant but unable to respond at the time due to driving demands.

The TDVM system may include the following components:

1. Analysis Software

This software may include a processing algorithm(s) designed to evaluate various driver prompts and response times. Evaluation of these response times may produce a probability factor associated with driver vigilance for each specific driver. Analysis capability of driver response times may be an important element of the system. Accuracy of vigilance probability outcome, clinical analysis and scientific validation associated with this process may determine effectiveness of the monitoring system.

2. Truck-cabin Steering-wheel Physiological Movement Transducer

This device may adapt to the truck steering wheel and provide output signals subject to a particular zone of the steering wheel, which has been activated by applying various degrees of pressure to the steering wheel.

3. Controller Unit & Monitoring Device (CU&MD)

This device may provide a communication link and data management for interfacing the truck's CU&MD to a remotely located monitoring station.

This device may also provide the transducer interface and transducer signal recording and detection capabilities.

This device may also output control to the driver indicator LEDS and record and transmit vigilance response times to the remote monitoring station.

4. Vigilance LED display

This device may be interfaced to the CU&MD unit and may provide visual response prompt to the truck driver.

5. Remote Recording, Monitoring and Analysis System

This system may facilitate a remote operators visual alarms when vigilance response times are outside acceptable thresholds.

This system may also provide communication links to the truck.

This system may also provide analysis and system reporting to allow real-time tracking of vigilance performance and vigilance alarm status.

Finally, it is to be understood that various alterations, modifications and/or additions may be introduced into the constructions and arrangements of parts previously described without departing from the spirit or ambit of the invention.

What is claimed is:

1. An apparatus for determining a vigilance state of a subject, said apparatus comprising:
   a first sensor capable of being operatively coupled to a subject wherein said first sensor monitors at least one physiological variable of said subject and provides a first output signal related to said at least one physiological variable;
   a second sensor capable of being operatively coupled to the subject and wherein said second sensor monitors the at least one physiological variable of said subject and provides a second output signal related to said at least one physiological variable of the subject;
   a computer processor for receiving said first and second output signals wherein said computer processor compares the first and second output signals to a reference data set, said reference data set being related to the at least one physiological variable of said subject and having been obtained when said subject is in a relaxed or a fatigued physiological state, to generate a data set representing a physiological state of said subject corresponding to said at least one physiological variable of the subject; and
   a threshold vigilance state signal set to a low vigilance state in the event that said data set decreases below a predetermined low vigilance state threshold value.

2. An apparatus according to claim 1 wherein one of said first sensor or said second sensor is operatively coupled to a select one member of the set comprising:
   a steering wheel; a gear shift structure; an interior portion of a seat for said subject; an exterior surface of the seat; a seat belt for said subject; an accelerator pedal; a clutch pedal; a brake pedal of the vehicle; the subject; a portion of clothing worn by the subject; a portion of protective gear worn by the subject; a portion of a corrective gear worn by the subject; a support structure; a bulkhead; a frame; a console; a mobile structure; an adjustable structure; a telescoping structure; a visor; a ceiling structure; a wall structure; a door structure; a mirror structure; a windscreen or a portion of a vehicle; and,
   wherein the other of said first sensor or said second sensor is operatively coupled to a second member, wherein said second member is different than said select one member, and said second member is selected from the set comprising:
     a steering wheel; a gear shift structure; an interior portion of a seat for said subject; an exterior surface of the seat; a seat belt for said subject; an accelerator pedal; a clutch pedal; a brake pedal of the vehicle; the subject; a portion of clothing worn by the subject; a portion of protective gear worn by the subject; a portion of a corrective gear worn by the subject; a support structure; a bulkhead; a frame; a console; a mobile structure; an adjustable structure; a telescoping structure; a visor; a ceiling structure; a wall structure; a door structure; a mirror structure; a windscreen or a portion of a vehicle.

3. An apparatus according to claim 1 wherein said at least one physiological variable comprises:
   a body movement signal; a body position signal; an electroencephalogram signal; an electromyographic signal; an eye opening sensor signal; an eye blink rate sensor signal; an eye movement sensor signal; an electrical skin resistance signal; a head movement signal; an eye position signal; an eye open versus closed ratio signal; a pulse signal; or a head position signal.

4. An apparatus according to claim 1 wherein at least one sensor is physically coupled to said subject or is disposed spaced from the subject and said at least one sensor further comprises:

a pressure transducer; a vibration sensor; a microphone; a contact switch; a capacitive static discharge material; a linear charge coupled device array; a two dimensional charge coupled device array; a photographic camera; a digital camera; a continuity circuit which is manually closed by contact from the subject; or a polyvinylidene fluoride material.

5. An apparatus according to claim 4 wherein the at least one sensor is coupled to a select one of the following set of elements: a portion of a steering wheel; a gear shift structure; a surface of a seat; an interior portion of a seat; a seat belt; an accelerator pedal; a clutch pedal; a brake pedal; a console; a dashboard; a bulkhead; a visor; a ceiling; a wall; a mobile structure; an adjustable structure; a telescoping structure; a door; a hatch; a window; a mirror; a piece of clothing worn by the subject; a piece of protective gear worn by the subject; a corrective device of the subject; or is disposed in view of the subject and coupled to a portion of a vehicle.

6. An apparatus according to claim 1 wherein said computer processor further comprises a digital processor.

7. An apparatus according to claim 1 wherein said threshold state signal is set to a low vigilance state pursuant to a vigilance algorithm operable by the computer processor.

8. An apparatus according to claim 7 wherein said vigilance algorithm is adapted to correlate said data set or apply a combinational logic sequence to said data set to detect a pattern in said data set which is associated with a vigilance state of the subject that is below said predetermined low vigilance state threshold value.

9. An apparatus according to claim 1, further comprising an intervention sequence module, wherein said intervention sequence module is coupled between the subject and at least one vehicle control input so that said subject has only partial control of said at least one vehicle control input, or wherein said intervention sequence module provides an alert signal to said subject in the event that the vigilance state of said subject is below said predetermined low vigilance state threshold value.

10. An apparatus according to claim 9 wherein said at least one vehicle control input comprises at least one of the set: a brake input; a fuel supply input; an accelerator input; a throttle input; a gear selector input; or a clutch input of a vehicle.

11. An apparatus according to claim 9 wherein said alert signal comprises at least one of:

an aerosol spray directed toward said subject;

an olfactory agent released in the presence of said subject a fluid spray directed toward said subject;

a vibration transducer coupled to a one of the following elements: a piece of clothing worn by the subject, the subject; a vehicle steering wheel; a seat belt for said subject; a seat for said subject; a floor area of the vehicle; an accelerator input structure; a brake input structure; a clutch input structure; a gear selection structure; a throttle selection structure; a console structure; a headrest structure; or a helmet structure worn by said subject;

an increased tension applied to said seat belt for said subject;

an audible signaling device; an alarm; a bell; a chime; a buzzer; a siren; a tone; a pre-recorded message; a radio; a music player; or a horn;

a rotary fan; a windscreen wiper; a source of illumination; a light emitting diode; a surface emitting diode; an information display; a hazard light set; or an instrument panel light;

opening a window; a hatch; or a port near the subject;

an increased intensity of illumination directed near the subject;

a flashing source of illumination near the subject;

a source of heated air introduced near the subject;

a source of cooled air introduced near the subject; or, an increase in an airflow directed toward the subject.

12. An apparatus according to claim 9 wherein said intervention sequence module further comprises a wireless communication system coupled to a remote monitoring station.

13. A method for determining a vigilance state of a subject, said method comprising the steps of:

monitoring at least one physiological variable of a subject by placing a plurality of sensors on a steering wheel of a vehicle, wherein each of said plurality of sensors provide a corresponding plurality of output signals;

deriving from said at least one physiological variable a data set representing at least one of a set of physiological states of said subject corresponding to the at least one physiological variable;

determining from said data set when a vigilance state of said subject crosses a predetermined vigilance threshold value by comparing the set of output signals from said plurality of sensors with a reference data set, wherein said reference data set includes information from said subject in a relaxed state or a fatigued state; and, providing a vigilance state output signal when the vigilance state of said subject crosses the predetermined vigilance threshold value.

14. A method according to claim 13 wherein said at least one physiological variable comprises at least one of the set of elements:

a body movement signal; a position signal; an acoustic signal, an electroencephalogram signal; an electromyographic signal; an eye opening sensor signal; an eye movement sensor signal; an eye blink rate sensor signal; an electrical skin resistance signal; a head movement signal; an eye position signal; an electrical skin resistance signal; a pulse signal; or a head position signal.

15. A method according to claim 13 wherein said step of monitoring further comprises a step of:

coupling at least one sensor to said subject either directly in physical contact with said subject or spaced from, but in view of, said subject;

and, wherein said at least one sensor further comprises at one of the following elements:

a pressure sensor; a capacitive static discharge material; a microphone, a charge coupled device; a video camera; a linear charge coupled device array; a two dimensional charge coupled device array; a photographic camera; a digital camera; a continuity circuit closed by manual contact from said subject; a pulse sensor; a galvanic skin resistance sensor; a skin impedance sensor; or a polyvinylidene fluoride material.

16. A method according to claim 15 wherein the at least one sensor is coupled to a one of the following elements:

a steering structure; a gear shift structure; an interior portion of a seat for said subject; an exterior surface of the seat; a seat belt for said subject; an accelerator pedal; a clutch pedal; a brake pedal; a throttle structure; the subject; a portion of clothing worn by the subject;

a portion of protective gear worn by the subject; a portion of a corrective gear worn by the subject; a support structure; a bulkhead; a frame; a console; a mobile structure; an adjustable structure; a telescoping structure; a visor; a ceiling structure; a wall structure; a door structure; a mirror structure; a windscreen or to a vehicle.

17. A method according to claim 13 wherein at least one of said step of deriving and said step of determining is performed by a digital computer processor.

18. A method according to claim 17 wherein said step of determining is performed by a vigilance algorithm operable by the digital computer processor.

19. A method according to claim 18 wherein said vigilance algorithm is adapted to correlate said data set or apply a combinational logic sequence to said data set to detect a pattern in said data set which is associated with a low vigilance state of the subject that is below said predetermined vigilance threshold value.

20. A method according to claim 13 further comprising the steps of:
intervening with a control input for a vehicle or alerting the subject via an alert signal, in the event that the vigilance state output signal of said subject is below said predetermined vigilance threshold value.

21. A method according to claim 20 wherein the step of intervening further comprises:
controlling application of a brake input;
cutting-off a vehicle fuel supply input;
reducing a vehicle fuel supply input;
reducing a yaw, pitch, roll or turn rate of said vehicle;
partially disabling an accelerator or throttle input structure;
fully disabling an accelerator or throttle input structure; or,
engaging a clutch input of said vehicle.

22. A method according to claim 20 wherein the step of alerting further comprises at least a one of:
applying a fluid spray toward the subject;
releasing an olfactory agent near the subject;
directing an aerosol spray toward the subject;
vibrating: a piece of clothing worn by the subject; the subject; a vehicle steering wheel; a seat belt for said subject; a seat for said subject; a floor area of the vehicle; an accelerator input structure; a brake input structure; a clutch input structure; a gear selection structure; a throttle selection structure; a console structure; a headrest structure; or a helmet structure worn by said subject;
activating: an audible signaling device; an alarm; a bell; a chime; a buzzer; a siren; a tone; a pre-recorded message; a radio; a music player; or a horn;
energizing a device near the subject wherein said device is a one of the set: a rotary fan; a windscreen wiper; a source of illumination; a light emitting diode; a surface emitting diode; an information display; a hazard light set; or an instrument panel display;
opening: a window; a hatch; or a port;
rapidly increasing illumination near the subject;
increasing ventilation near the subject; or changing the temperature near the subject.

23. A method according to claim 20 wherein the step of intervening further comprises transmitting a signal from said vehicle to a remote monitoring station via a wireless communication system.

24. An apparatus for determining a vigilance state of a subject, said apparatus comprising:
at least one sensor operatively coupled to a subject wherein said at least one sensor monitors at least one physiological variable of said subject and provides a first output signal related to said at least one physiological variable;
a computer processor coupled to said first output signal wherein said computer processor applies a select criteria to said first output signal and generates a data set representing a physiological state of said subject corresponding to said at least one physiological variable of the subject; and
a threshold vigilance state signal set to a low vigilance state in the event that said data set decreases below a predetermined low vigilance state threshold value,
said low vigilance state being set pursuant to a vigilance algorithm operable by the computer processor, said vigilance algorithm being adapted to correlate said data set or apply a combinational logic sequence to said data set to detect a pattern in said data set which is associated with a vigilance state of the subject that is below said predetermined low vigilance state threshold value,
said vigilance algorithm further comprising at least one look up table and said at least one look up table including a reference movement data set correlated to a set of vigilance states with a first one of said set of vigilance states above said predetermined low vigilance state threshold value and a second one of said set of vigilance states below said predetermined low vigilance state threshold value.

25. An apparatus for determining a vigilance state of a subject, said apparatus comprising:
at least one sensor operatively coupled to a subject wherein said at least one sensor monitors at least one physiological variable of said subject and provides a first output signal related to said at least one physiological variable;
a computer processor coupled to said first output signal wherein said computer processor applies a select criteria to said first output signal and generates a data set representing a physiological state of said subject corresponding to said at least one physiological variable of the subject; and
a threshold vigilance state signal set to a low vigilance state in the event that said data set decreases below a predetermined low vigilance state threshold value,
said low vigilance state being set pursuant to a vigilance algorithm operable by the computer processor, said vigilance algorithm providing a vigilance state probability factor output as a function of a weighted set of movement data values.

26. A method for determining a vigilance state of a subject, said method comprising the steps of:
monitoring at least one physiological variable of a subject;
deriving from said at least one physiological variable a data set representing a one of a set of physiological states of said subject corresponding to the at least one physiological variable;
determining from said data set when a vigilance state of said subject crosses a predetermined vigilance threshold value; and,
providing a vigilance state output signal when the vigilance state of said subject crosses the predetermined vigilance threshold value;

wherein at least said step of determining is performed by a digital computer processor, said step of determining being performed by a vigilance algorithm operable by the digital computer processor, and wherein said vigilance algorithm is adapted to correlate said data set or apply a combinational logic sequence to said data set to detect a pattern in said data set which is associated with a low vigilance state of the subject that is below said predetermined vigilance threshold value; and wherein said vigilance algorithm incorporates at least one look up table which comprises a reference movement data set and a set of vigilance states with one state of said set of vigilance states above said predetermined low vigilance state threshold value and another state of said set of vigilance states below said predetermined low vigilance state threshold value.

27. A method for determining a vigilance state of a subject, said method comprising the steps of:

monitoring at least one physiological variable of a subject;

deriving from said at least one physiological variable a data set representing a one of a set of physiological states of said subject corresponding to the at least one physiological variable;

determining from said data set when a vigilance state of said subject crosses a predetermined vigilance threshold value; and, providing a vigilance state output signal when the vigilance state of said subject crosses the predetermined vigilance threshold value;

wherein at least said step of determining is performed by a digital computer processor, said step of determining being performed by a vigilance algorithm operable by the digital computer processor, said vigilance algorithm being adapted to determine a vigilance probability factor output as a function of a weighted set of movement data values.

* * * * *